US010975098B2

(12) United States Patent
Wang et al.

(10) Patent No.: US 10,975,098 B2
(45) Date of Patent: Apr. 13, 2021

(54) SUBSTITUTED AMINOTHIAZOLOPYRIMIDINEDIONES FOR THE TREATMENT OF VIRUS INFECTION

(71) Applicant: Hoffmann-La Roche Inc., Little Falls, NJ (US)

(72) Inventors: Lisha Wang, Riehen (CH); Hongying Yun, Shanghai (CN); Xiufang Zheng, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/816,940

(22) Filed: Mar. 12, 2020

(65) Prior Publication Data

US 2020/0231600 A1   Jul. 23, 2020

Related U.S. Application Data

(60) Division of application No. 15/852,108, filed on Dec. 22, 2017, now Pat. No. 10,590,146, which is a continuation of application No. PCT/EP2016/064771, filed on Jun. 27, 2016.

(30) Foreign Application Priority Data

Jun. 30, 2015 (WO) ................ PCT/CN2015/082844

(51) Int. Cl.
| | | |
|---|---|---|
| *C07D 513/04* | (2006.01) | |
| *A61K 31/519* | (2006.01) | |
| *C07H 1/00* | (2006.01) | |
| *C07H 19/24* | (2006.01) | |
| *A61P 31/20* | (2006.01) | |

(52) U.S. Cl.
CPC .......... *C07D 513/04* (2013.01); *A61K 31/519* (2013.01); *A61P 31/20* (2018.01); *C07H 1/00* (2013.01); *C07H 19/24* (2013.01)

(58) Field of Classification Search
CPC .................................................. C07D 513/04
See application file for complete search history.

(56) References Cited

U.S. PATENT DOCUMENTS

| | | |
|---|---|---|
| 5,476,659 A | 12/1995 | Goodman et al. |
| 7,560,544 B2 | 7/2009 | Webber et al. |
| 7,709,448 B2 | 5/2010 | Haley et al. |
| 9,061,041 B2 | 6/2015 | Girijavallabhan et al. |
| 10,590,146 B2 | 3/2020 | Wang et al. |
| 2005/0004144 A1 | 1/2005 | Carson et al. |
| 2016/0008374 A1 | 1/2016 | Geleziunas et al. |

FOREIGN PATENT DOCUMENTS

| | | |
|---|---|---|
| EP | 0343945 A2 | 11/1989 |
| EP | 1072607 A2 | 1/2001 |
| WO | 89/05649 A1 | 6/1989 |
| WO | 98/16184 A2 | 4/1998 |
| WO | 2005/016235 A2 | 2/2005 |
| WO | 2005/025583 A2 | 3/2005 |
| WO | 2006/066080 A1 | 6/2006 |
| WO | 2007/135134 A1 | 11/2007 |
| WO | 2007/150002 A2 | 12/2007 |
| WO | 2008/011406 A2 | 1/2008 |
| WO | 2008/140549 A1 | 11/2008 |
| WO | 2009/026292 A1 | 2/2009 |
| WO | 2016/091698 A1 | 6/2016 |

OTHER PUBLICATIONS

Asselah, T., et al., "Interferon therapy for chronic hepatitis B" Clin Liver Dis 11(4):839-849 (Nov. 1, 2007).
Connolly, D., et al., "New developments in Toll-like receptor targeted therapeutics" Curr Opin Pharmacol 12(4):510-518 (Aug. 1, 2012).
Gane, E., et al., "Safety and pharmacodynamics of oral TLR-7 agonist GS-9620 in patients with chronic hepatitis B" Abstract Ann. Meeting Am. Assoc. Study Liver Dis, Washington, D.C., pp. 661A, Abstract 946 ( Nov. 2013).
Hemmi, H., et al., "Small anti-viral compounds activate immune cells via the TLR7 MyD88-dependent signaling pathway" Nat Immunol 3(2):196-200 (Jan. 22, 2002).
ISR for PCT/EP2016/064771 (dated Aug. 12, 2016).
Kaisho, T., et al., "Turning NF-kB and IRFs on and off in DC" Trends Immunol 29(7):329-336 (Jul. 1, 2008).
Roethle, P., et al., "Identification and Optimization of Pteridinone Toll-like Receptor 7 (TLR7) Agonists for the Oral Treatment of Viral Hepatitis" J Med Chem 56(18):7324-7333 (Sep. 26, 2013).

*Primary Examiner* — Brian E McDowell
(74) *Attorney, Agent, or Firm* — Genentech, Inc.; Richard G. A. Bone

(57) ABSTRACT

The present invention relates to compounds of formula (I), (I)

wherein $R^1$ to $R^4$ are as described herein, and their prodrugs or pharmaceutically acceptable salt, enantiomer or diastereomer thereof, and compositions including the compounds and methods of using the compounds.

13 Claims, No Drawings

SUBSTITUTED AMINOTHIAZOLOPYRIMIDINEDIONES FOR THE TREATMENT OF VIRUS INFECTION

CLAIM OF PRIORITY

The present application is a divisional of U.S. application Ser. No. 15/852,108, which is a continuation of international patent application serial no. PCT/EP2016/064771, which claims benefit of priority to China application no. PCT/CN2015/082844, all of which applications are hereby incorporated by reference in their respective entireties.

TECHNICAL FIELD

The present invention relates to novel substituted aminothiazolopyrimidinedione and their corresponding derivatives that have Toll-like receptor agonism activity and their prodrugs thereof, as well as their manufacture, pharmaceutical compositions containing them and their potential use as medicaments.

BACKGROUND

The present invention relates to compounds of formula (I) and (Ia),

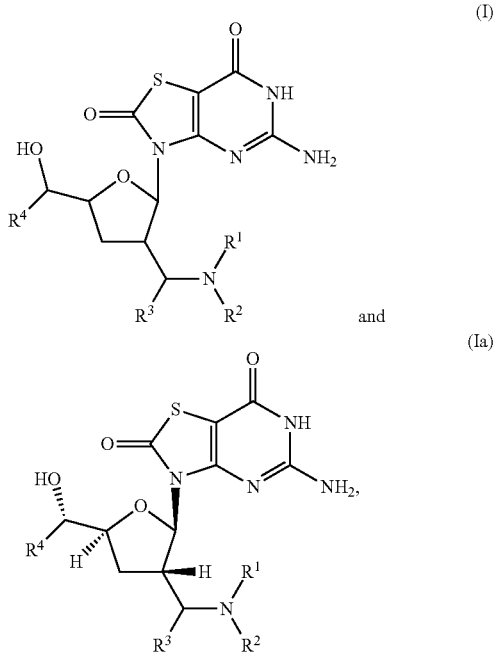

wherein $R^1$ to $R^4$ are described below, or pharmaceutically acceptable salt, enantiomer or diastereomer thereof.

Toll-like receptors (TLRs) recognize a wide range of conserved pathogen-associated molecular patterns (PAMPs). They play important roles of sensing invading pathogens and subsequent initiation of innate immune responses. There are 10 known members of the TLR family in human, which are type I transmembrane proteins featuring an extracellular leucine-rich domain and a cytoplasmic tail that contains a conserved Toll/interleukin (IL)-1 receptor (TIR) domain. Both TLR7 and TLR8 are localised intracellularly to the endosomal membrane. They are phylogenetically similar and are both capable of recognizing single-stranded RNA (ssRNA) and short double-stranded RNA, due to their roles in sensing different viral pathogens. TLR7 and TLR8 also can be stimulated with oligoribonucleotides and a variety of synthetic chemical agonists such as imidazoquinolines. Following binding of ssRNA or small molecules to TLR7 and/or TLR8, the receptor in its dimerized form is believed to undergo a structural change leading to the subsequent recruitment of adapter proteins at its cytoplasmic domain, including the myeloid differentiation primary response gene 88 (MyD88). Following the initiation of the receptor signalling cascade via the MyD88 pathway, cytoplasmic transcription factors such as interferon regulatory factor 7 (IRF-7) by TLR7 and/or nuclear factor kappa B (NF-κB) by TLR8 are activated. These transcription factors then translocate into the nucleus and initiate the activation of various genes, e.g., type I interferon (IFN-α and IFN-β) and other pro-inflammatory cytokine genes, e.g. IL-6, TNFα et al.

TLR8 is known to be primarily expressed in monocytes/macrophages and myeloid dendritic cells (mDCs), while TLR7 is predominately expressed in plasmacytoid DCs (pDCs) and, to some extent, in B cells and monocytes/macrophages. The TLR7 or TLR8 selective agonist can activate different cell types and induce different immune response. However, a TLR7/8 dual agonist has the potential to activate induce broad immune response. Because of their efficiency in activating immune responses, the TLR7 and/or TLR8 agonists are being investigated for a broad variety of applications, including antiviral and antitumor therapies and use as a vaccine adjuvant.

Several TLR7 and/or TLR8 agonists have been used for therapeutic purposes. Imiquimod (ALDARA™) is a U.S. FDA approved TLR7 agonist drug for topical use to treat skin lesions due to human papillomavirus infection. The TLR7/8 dual agonist Resiquimod (R-848) and the TLR7 agonist 852A are under evaluating for treating human genital herpes and chemotherapy-refractory metastatic melanoma, respectively. ANA773 is an oral pro-drug TLR7 agonist, developed for the treatment of patients with chronic hepatitis C virus (HCV) infection and chronic hepatitis B infection. GS-9620 is an orally available TLR7 agonist. A phase Ib study demonstrated that treatment with GS-9620 was safe, well tolerated and resulted in dose-dependent ISG15 mRNA induction in patients with chronic hepatitis B (E. J. Gane et al, Annu Meet Am Assoc Study Liver Dis (November 1-5, Washington, D.C.) 2013, Abst 946). More recently, VTX-2337, a highly selective TLR8 agonist, discovered by VentiRX Pharmaceuticals (WO 2007024612), has been used in treatment of human head and neck cancer patients. (D. W. Northfelt et al, Clin Cancer Res 2014, 20, 3683-3691.) Although quite a few TLR7 agonists have been reported in the last decade, and only few TLR8 or TLR7/8 dual agonists were reported, there is still high unmet clinical need for developing potent and safe TLR7 and/or TLR8 agonists as new antiviral and antitumor treatment to offer more therapeutic solutions or replace existing partly effective treatments.

SUMMARY

The present invention provides a series of novel 3-substituted 5-amino-6H-thiazolo[4,5-d]pyrimidine-2,7-dione compounds, that have Toll-like receptor agonism activity and their prodrugs. The invention also provides the bioactivity of such compounds to induce SEAP level increase by activating Toll-like receptors, such as TLR7 and/or TLR8 receptors, the metabolic conversion of prodrugs to parent compounds in the presence of human hepatocytes, and the therapeutic or prophylactic use of such compounds and their pharmaceutical compositions comprising these compounds and their prodrugs to treat or prevent diseases such as cancer, autoimmune diseases, inflammation, sepsis, allergy, asthma, graft rejection, graft-versus-host disease, immunodeficiencies, and infectious diseases like HBV or HCV. The present invention also provides compounds with superior activity.

The present invention relates to novel compounds of formula (I) and (Ia),

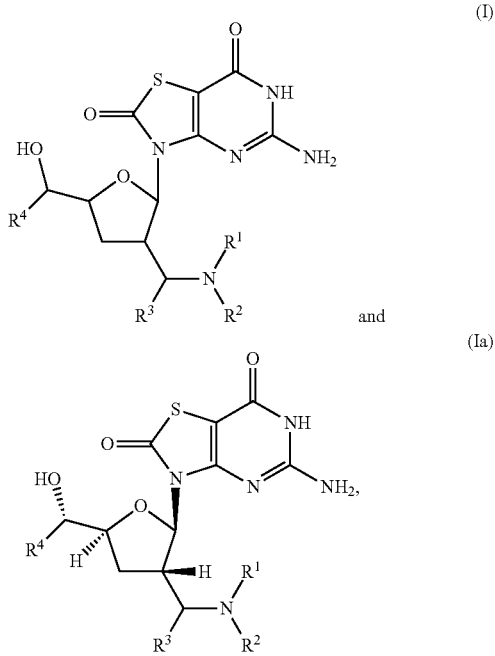

wherein
$R^1$ is H, $C_{1-6}$alkyl, $C_{3-7}$cycloalkyl or phenyl$C_{1-6}$alkyl, said phenyl$C_{1-6}$alkyl being unsubstituted or substituted with one to three substituents independently selected from $C_{1-6}$alkyl and halogen;
$R^2$ is H or $C_{1-6}$alkyl;
$R^3$ is $C_{1-6}$alkyl;
$R^4$ is $C_{1-6}$alkyl;
or pharmaceutically acceptable salt, enantiomer or diastereomer thereof.

The invention also relates to their manufacture, medicaments based on a compound in accordance with the invention and their production as well as the use of compounds of formula (I) or (Ia) or their prodrugs, thereof as TLR7 and/or TLR8 agonist. Accordingly, the compounds of formula (I) and (Ia) are useful for the antiviral treatment or prophylaxis, such as HBV and/or HCV infection, as well as antitumor treatment, with Toll-like receptors agonism.

DETAILED DESCRIPTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

Definitions

As used herein, the term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, iso-butyl, tert-butyl and the like. Particular "$C_{1-6}$alkyl" groups are methyl, ethyl and n-propyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" group is cyclopropyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) or (Ia) and their prodrugs which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The compounds of the invention may exhibit the phenomenon of tautomerism. While the formula drawings cannot expressly depict all possible tautomeric forms, it is to be understood they are intended to represent any tautomeric form of the depicted compound and are not to be limited merely to a specific compound form depicted by the formula drawings. For example, it is understood for formula (II) that regardless of whether or not the substituents are shown in their enol or their keto form, they represent the same compound (as shown in the example below).

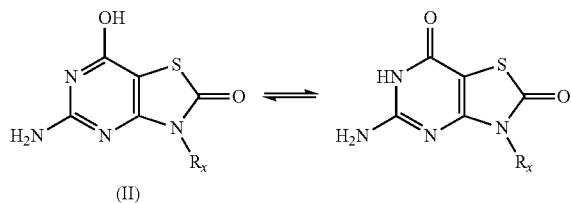

$R_x$ refers to any feasible substituent.

Some of the compounds of the present invention may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form. As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.). Additionally, compounds of formula (I) and (Ia) and their prodrugs, formula (II) and (IIa), and other compounds of the invention are intended to cover solvated as well as unsolvated forms of the identified structures. For example, formula (I) or (Ia) includes compounds of the indicated structure in both hydrated and non-hydrated forms. Other examples of solvates include the structures in combination with isopropanol, ethanol, methanol, DMSO, ethyl acetate, acetic acid, or ethanolamine.

The term "prodrug" denotes a form or derivative of a compound which is metabolized in vivo, e.g., by biological fluids or enzymes by a subject after administration, into a pharmacologically active form of the compound in order to produce the desired pharmacological effect. Prodrugs are described e.g. in "The Organic Chemistry of Drug Design and Drug Action", by Richard B. Silverman, Academic Press, San Diego, 2004, Chapter 8 Prodrugs and Drug Delivery Systems, pp. 497-558.

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

TLR7 and/or TLR8 Agonist

The present invention relates to a compound of formula (I),

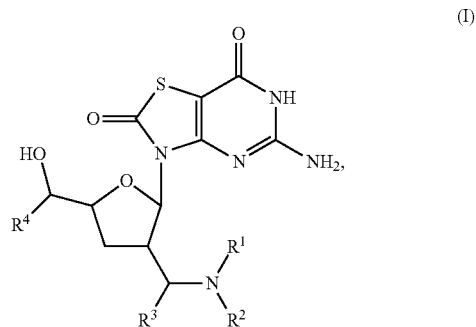

wherein
$R^1$ is H, $C_{1-6}$alkyl, $C_{3-7}$cycloalkyl or phenyl$C_{1-6}$alkyl, said phenyl$C_{1-6}$alkyl being unsubstituted or substituted with one to three substituents independently selected from $C_{1-6}$alkyl and halogen;
$R^2$ is H or $C_{1-6}$alkyl;
$R^3$ is $C_{1-6}$alkyl;
$R^4$ is $C_{1-6}$alkyl;
or pharmaceutically acceptable salt, enantiomer or diastereomer thereof.

Another embodiment of present invention is relates to (ii) a compound of formula (Ia),

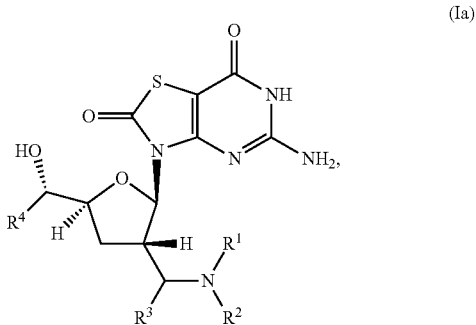

wherein
R¹ is H, C₁₋₆alkyl, C₃₋₇cycloalkyl or phenylC₁₋₆alkyl, said phenyl C₁₋₆alkyl being unsubstituted or substituted with one to three substituents independently selected from C₁₋₆alkyl and halogen;
R² is H or C₁₋₆alkyl;
R³ is C₁₋₆alkyl;
R⁴ is C₁₋₆alkyl;
or pharmaceutically acceptable salt, enantiomer or diastereomer thereof.

A further embodiment of present invention is (iii) a compound of formula (I) or (Ia), wherein
R¹ is H, methyl, propyl, cyclopropyl, benzyl, fluorobenzyl, chlorobenzyl, fluorochlorobenzyl or methylbenzyl;
R² is H or methyl;
R³ is methyl;
R⁴ is ethyl;
or pharmaceutically acceptable salt, enantiomer or diastereomer thereof.

A further embodiment of present invention is (iv) a compound of formula (I) or (Ia), wherein R¹ is H, C₁₋₆alkyl or phenylC₁₋₆alkyl; or pharmaceutically acceptable salt, enantiomer or diastereomer thereof.

A further embodiment of present invention is (v) a compound of formula (I) or (Ia), wherein R¹ is H, methyl or benzyl; or pharmaceutically acceptable salt, enantiomer or diastereomer thereof.

A further embodiment of present invention is (vi) a compound of formula (I) or (Ia), wherein R² is H; or pharmaceutically acceptable salt, enantiomer or diastereomer thereof.

Another embodiment of present invention is that (vii) particular compounds of formula (I) or (Ia) are the following:
5-Amino-3-[(2R,3S,5S)-3-[(1S)-1-aminoethyl]-5-[(1S)-1-hydroxypropyl]tetrahydrofuran-2-yl]-6H-thiazolo[4,5-d]pyrimidine-2,7-dione;
5-amino-3-[(2R,3S,5S)-3-[(1R)-1-aminoethyl]-5-[(1S)-1-hydroxypropyl]tetrahydrofuran-2-yl]-6H-thiazolo[4,5-d]pyrimidine-2,7-dione;
5-Amino-3-[(2R,3S,5S)-5-[(1S)-1-hydroxypropyl]-3-[(1R)-1-(methyl amino)ethyl]tetrahydrofuran-2-yl]-6H-thiazolo[4,5-d]pyrimidine-2,7-dione;
5-Amino-3-[(2R,3S,5S)-5-[(1S)-1-hydroxypropyl]-3-[(1R)-1-(propylamino)ethyl]tetrahydrofuran-2-yl]-6H-thiazolo[4,5-d]pyrimidine-2,7-dione;
5-Amino-3-[(2R,3S,5S)-3-[(1R)-1-(cyclopropylamino)ethyl]-5-[(1S)-1-hydroxypropyl]tetrahydrofuran-2-yl]-6H-thiazolo[4,5-d]pyrimidine-2,7-dione;
5-Amino-3-[(2R,3S,5S)-3-[(1R)-1-(benzylamino)ethyl]-5-[(1S)-1-hydroxypropyl]tetrahydrofuran-2-yl]-6H-thiazolo[4,5-d]pyrimidine-2,7-dione;
5-Amino-3-[(2R,3S,5S)-5-[(1S)-1-hydroxypropyl]-3-[(1S)-1-(methylamino)ethyl]tetrahydrofuran-2-yl]-6H-thiazolo[4,5-d]pyrimidine-2,7-dione;
5-Amino-3-[(2R,3S,5S)-3-[(1S)-1-(benzylamino)ethyl]-5-[(1S)-1-hydroxypropyl]tetrahydrofuran-2-yl]-6H-thiazolo[4,5-d]pyrimidine-2,7-dione; and
5-Amino-3-[(2R,3S,5S)-3-[(1R)-1-(dimethylamino)ethyl]-5-[(1S)-1-hydroxypropyl]tetrahydrofuran-2-yl]-6H-thiazolo[4,5-d]pyrimidine-2,7-dione;
or a pharmaceutically acceptable salt, enantiomer, or diastereomer thereof.

Synthesis

The compounds of the present invention are prepared by any conventional means. Suitable processes for synthesizing these compounds as well as their starting materials are provided in the schemes below and in the examples. All substituents, in particular, R¹ to R⁴ are as defined above unless otherwise indicated. Furthermore, and unless explicitly otherwise stated, all reactions, reaction conditions, abbreviations and symbols have the meanings well known to a person of ordinary skill in organic chemistry.

Scheme 1

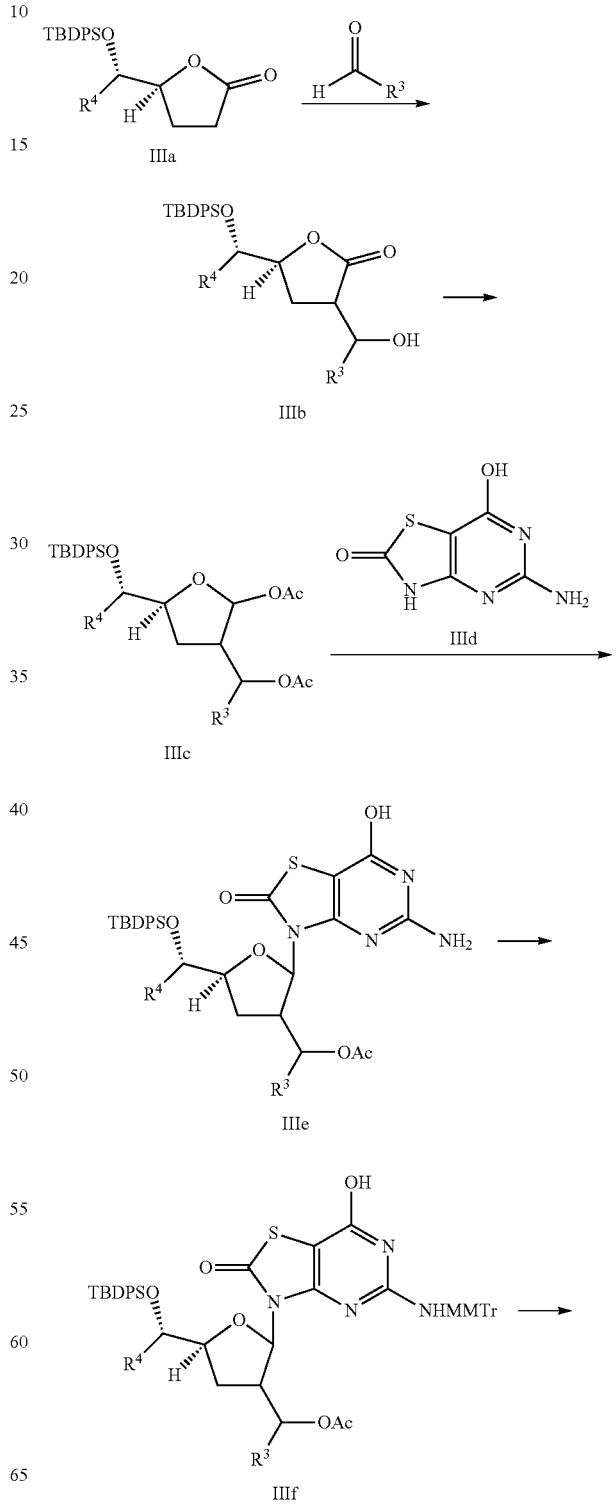

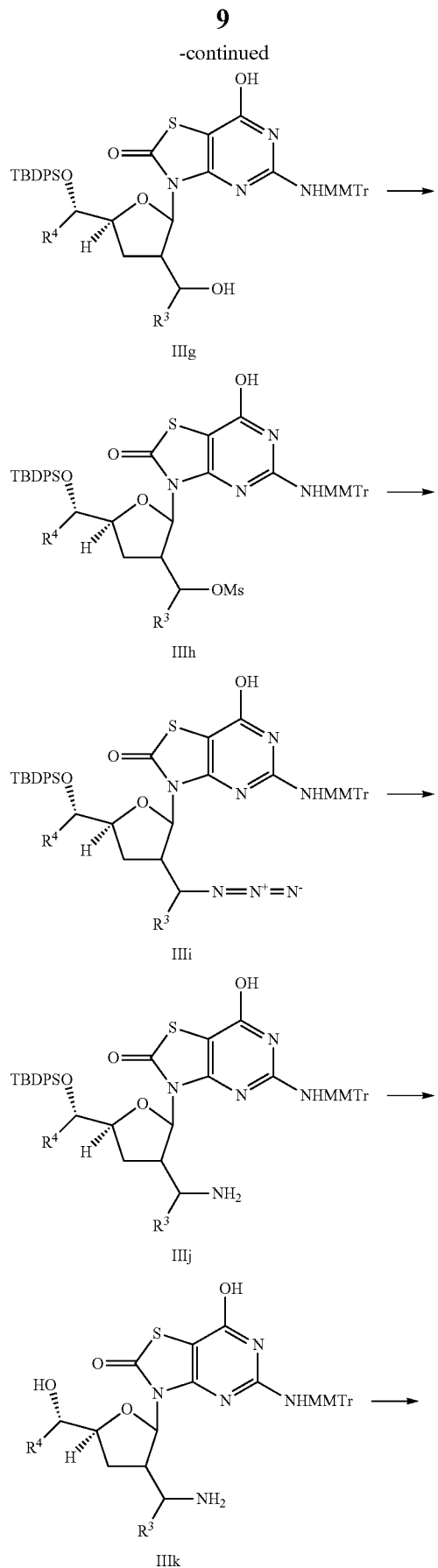

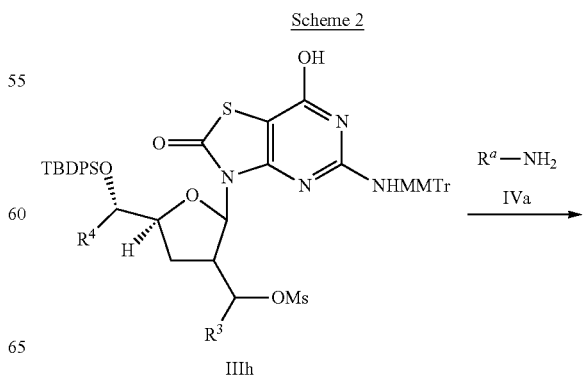

Compound of interest IIIm can be prepared according to Scheme 1. Aldol condensation of lactone IIIa with aldehydes and a suitable base, such as lithium diisopropylamide and lithium bis(trimethylsilyl)azanide, affords compound IIIb. The reaction can also be carried out in the presence of Lewis acid additive such as zinc bromide and cerium(III) chloride. Compound IIIb can be reduced by a reducing agent, such as diisobutyl aluminium hydride, followed by further protection of hydroxyl group with a protecting agent, such as acetyl chloride and acetic anhydride, to give the key intermediate IIIc. Coupling of compound IIIc with compound IIId in the presence of an appropriate silyl ether protecting agent, such as N,O-bis(trimethylsilyl)acetamide and hexamethyldisilazane, and a suitable Lewis acid, such as trimethylsilyl trifluoromethanesulfonate, trimethylsilyl iodide, tin (IV) chloride and titanium tetrachloride, to afford compound IIIe. Compound IIIe is converted to compound IIIf by introduction of 4-methoxytriphenylmethyl protecting group. Deprotection of compound IIIf affords compound IIIg, followed by mesylation with mesylating reagent, such as methanesulfonyl chloride, to give compound IIIh, followed by substitution reaction with sodium azide to afford compound IIIi. Reduction of compound IIIi gives compound IIIj with reducing agent, such as Zinc powder in acetic acid. Deprotection of compound IIIj in the presence of an appropriate fluoride reagent, such as tetrabutylammonium fluoride and ammonium fluoride, affords compound IIIk, which can be converted to the final compound IIIm by deprotection with a suitable acid, such as formic acid.

Scheme 2

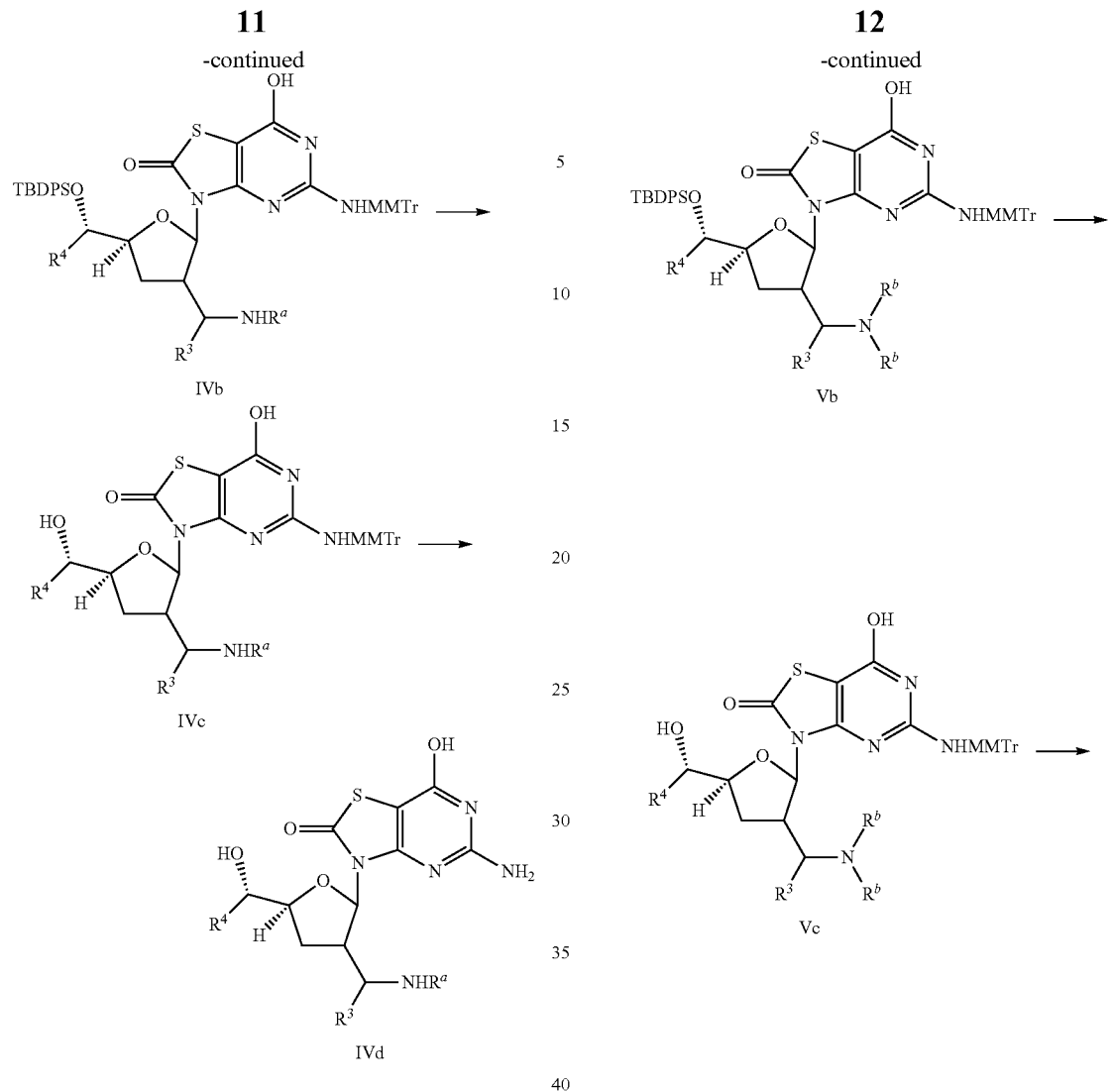

$R^a$ is $R^1$ or $R^2$.

Compound of interest IVd is prepared according to Scheme 2. Substitution of compound IIIh with various amine IVa gives compound IVb. Deprotection of compound IVb in the presence of an appropriate fluoride reagent, such as tetrabutylammonium fluoride and ammonium fluoride, affords compound IVc. Compound IVc is converted to the final compound IVd by deprotection with a suitable acid, such as formic acid.

Scheme 3

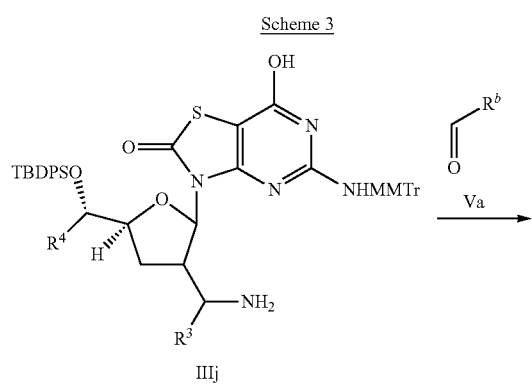

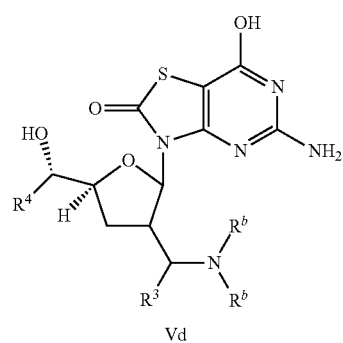

$R^b$ is $C_{1-6}$alkyl.

Compound of interest Vd is prepared according to Scheme 3. Direct reductive amination of amine in compound IIIj with aldehyde Va in the presence of a suitable reducing agent such as $NaBH(OAc)_3$ gives compound Vb. Deprotection of compound Vb in the presence of an appropriate fluoride reagent such as tetrabutylammonium fluoride or ammonium fluoride affords compound Vc, which is converted to the final compound Vd by deprotection with a suitable acid, such as formic acid.

This invention also relates to a process for the preparation of a compound of formula (I) or (Ia) comprising the reaction of:
(a) the reaction of a compound of formula (IIIk),

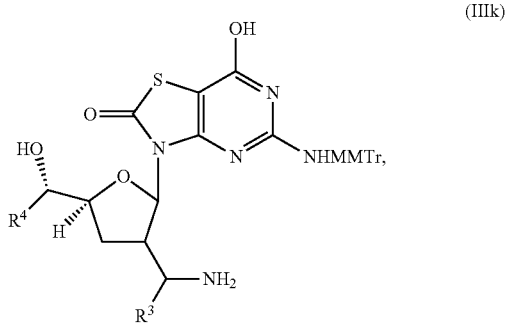

with an acid;
(b) the reaction of a compound of formula (IVc),

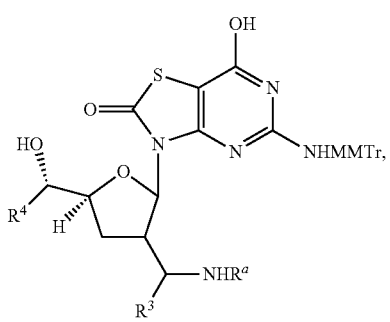

with an acid, wherein $R^a$ is $R^1$ or $R^2$;
(c) the reaction of a compound of formula (Vc),

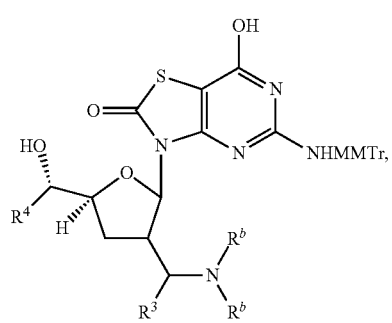

with an acid, wherein $R^b$ is $C_{1-6}$alkyl;
or wherein $R^a$, $R^b$, $R^3$, $R^4$ are defined above.

In step (a), (b) and (c), the acid can be for example formic acid.

A compound of formula (I) or (Ia) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) or (Ia) or their prodrugs may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) or (Ia) or their prodrugs are formulated in an acetate buffer, at pH 5. In another embodiment, the compounds of formula (I) or (Ia) or their prodrugs are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to activate TLR7 and/or TLR8 receptors and lead to produce type I interferon (IFN-α and IFN-β) and other pro-inflammatory cytokine genes, which is able to be used be used, but not limited, for the antiviral and antitumor treatment or prevention.

In one example, the pharmaceutically effective amount of the compound of the invention administered parenterally per dose will be in the range of about 0.1 to 50 mg/kg, alternatively about 0.1 to 30 mg/kg of patient body weight per day, with the typical initial range of compound used being 0.3 to 15 mg/kg/day. In another embodiment, oral unit dosage forms, such as tablets and capsules, preferably contain from about 20 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems, Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 20 to 1000 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 20 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I) or (Ia) or their prodrugs, or pharmaceutically acceptable salts or enantiomers or diastereomers thereof.

In a further embodiment includes a pharmaceutical composition comprising a compound of formula (I) or (Ia) or their prodrugs, or pharmaceutically acceptable salts or enantiomers or diastereomers thereof, together with a pharmaceutically acceptable carrier or excipient.

Another embodiment includes a pharmaceutical composition comprising a compound of formula (I) or (Ia) or their prodrugs, or pharmaceutically acceptable salts or enantiomers or diastereomers thereof for use in the treatment of cancer or hepatitis B virus infection.

Indications and Methods of Treatment

The present invention provides methods for treating or preventing cancer, or a hepatitis B viral infection and/or hepatitis C viral infection in a patient in need thereof.

The present invention further provides methods for introducing a therapeutically effective amount of a formula (I) or (Ia) compounds or their prodrugs, or other compounds of the invention into the blood stream of a patient in the treatment and/or prevention of cancer, or hepatitis B and/or C viral infection.

The methods of the present invention are particularly well suited for human patients. In particular, the methods and doses of the present invention can be useful for, but not limited to, cancer, HBV and/or HCV infected patients. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Another embodiment includes a method of treating or preventing cancer, or hepatitis B viral infection and/or hepatitis C viral infection in a mammal in need of such treatment, wherein the method comprises administering to said mammal a therapeutically effective amount of a compound of formula (I) or (Ia) or their prodrugs, or enantiomers, diastereomers, prodrugs or pharmaceutically acceptable salts thereof.

EXAMPLES

The invention will be more fully understood by reference to the following examples. They should not, however, be construed as limiting the scope of the invention.

Abbreviations
ACN: acetonitrile
BSA: N, O-bis(trimethylsilyl)acetamide
DIBAL-H: diisobutyl aluminium hydride
DMAP: 4-dimethylaminopyridine
DCM: dichloromethane
$EC_{50}$: the molar concentration of an agonist, which produces 50% of the maximum possible response for that agonist.
EtOAc: ethyl acetate
FBS: fetal bovine serum
HPLC: high performance liquid chromatography
LDA: lithium diisopropylamide
MMTrCl: 4-methoxytriphenylmethyl chloride
MS (ESI): mass spectroscopy (electron spray ionization)
obsd.: observed
SFC: supercritical fluid chromatography
TBAF: tetrabutylammonium fluoride
THF: tetrahydrofuran
TBDPSCl: tert-butylchlorodiphenylsilane
TMSOTf: trimethylsilyl trifluoromethanesulfonate
v/v: volume ratio General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 m, OBD™ 30×100 mm) column or SunFire™ Perp $C_{18}$ (5 μm, OBD™ 30×100 mm) column.

Chiral Separation was conducted on Thar 350 preparative SFC using ChiralPak AD-10μ (200×50 mm I.D.) with mobile phase A for $CO_2$ and B for ethanol. LC/MS spectra were obtained using a Waters UPLC-SQD Mass. Standard LC/MS conditions were as follows (running time: 3 minutes):

Acidic condition: A: 0.1% formic acid and 1% acetonitrile in $H_2O$; B: 0.1% formic acid in acetonitrile;

Basic condition: A: 0.05% $NH_3.H_2O$ in $H_2O$; B: acetonitrile.

Mass spectra (MS): generally only ions which indicate the parent mass are reported, and unless otherwise stated the mass ion quoted is the positive mass ion $(M+H)^+$.

NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

Example 1

5-Amino-3-[(2R,3S,5S)-3-[(1S)-1-aminoethyl]-5-[(1S)-1-hydroxypropyl]tetrahydrofuran-2-yl]-6H-thiazolo[4,5-d]pyrimidine-2,7-dione (Example 1-A) and 5-amino-3-[(2R,3S,5S)-3-[(1R)-1-aminoethyl]-5-[(1S)-1-hydroxypropyl]tetrahydrofuran-2-yl]-6H-thiazolo[4,5-d]pyrimidine-2,7-dione (Example 1-B)

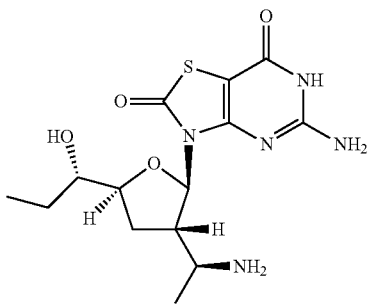

1-A

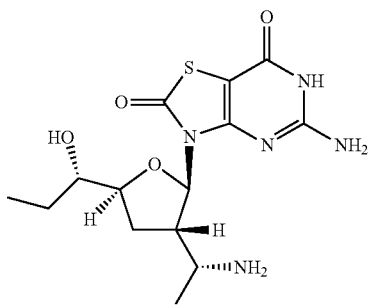

1-B

Preparation of (2S)-5-oxotetrahydrofuran-2-carboxylic acid

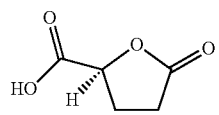

1a (2S)-2-Aminopentanedioic acid (2.50 kg, 16.99 mol) was dissolved in $H_2O$ (6 L) and concentrated HCl (3.5 L), then a solution of $NaNO_2$ (1.76 kg, 25.49 mol) in $H_2O$ (5 L) was added to previous solution slowly at −5° C. to 0° C. After addition, the reaction mixture was stirred at 28° C. for 16 hours, then the reaction mixture was concentrated below 50° C. to give a residue, which was suspended in ethyl acetate (5 L). After filtration, the filtrate was dried over anhydrous $Na_2SO_4$ and concentrated in vacuo to give 1.5 kg of (2S)-5-oxotetrahydrofuran-2-carboxylic acid as a colorless oil which was used in the next step without further purification.

Preparation of (2S)-5-oxotetrahydrofuran-2-carbonyl chloride

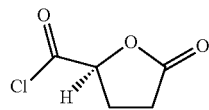

1b

To a mixture of (2S)-5-oxotetrahydrofuran-2-carboxylic acid (1.00 kg, 7.69 mol) in DCM (10.0 L) and DMF (10.0 mL) was added $(COCl)_2$ (2.93 kg, 23.06 mol) dropwise and slowly at 0° C. under $N_2$. The reaction was stirred at 0° C. for 30 minutes, then heated to 25° C. and stirred for further 2 hours. After the reaction was completed, the reaction mixture was concentrated in vacuo at 40° C. to afford 1.0 kg of (2S)-5-oxotetrahydrofuran-2-carbonyl chloride as a yellow oil, which was used in the next step without further purification.

Preparation of (5S)-5-propanoyltetrahydrofuran-2-one

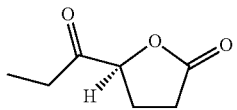

1c

To a solution of (2S)-5-oxotetrahydrofuran-2-carbonyl chloride (1.00 kg, 6.73 mol) in THF (5.0 L) was added bromo(ethyl)magnesium (2.24 L, 6.73 mol) dropwise at −78° C. under $N_2$. After the addition, the reaction mixture was stirred at −78° C. for 3 hours. Then the reaction mixture was poured into saturated $NH_4Cl$ solution (100 mL), then extracted with ethyl acetate, dried over anhydrous $Na_2SO_4$, filtered and concentrated in vacuo. The residue was purified by column chromatography (eluting with 10-50% ethyl acetate in petroleum ether) to give 500 g of (5S)-5-propanoyltetrahydrofuran-2-one as a light yellow oil.

Preparation of (5S)-5-[(1S)-1-hydroxypropyl]tetrahydrofuran-2-one

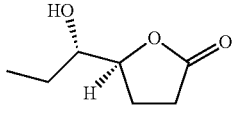

1d

To a solution of (5S)-5-propanoyltetrahydrofuran-2-one (1.50 kg, 10.55 mol) in THF (15.0 L) was added K-selectride (2.34 kg, 10.55 mol) dropwise at −78° C. under $N_2$. The reaction mixture was stirred at −78° C. for 3 hours. The resulting mixture was poured into a cold aqueous $NaHCO_3$ solution (15 L) and stirred for 12 hours. The aqueous phase was extracted with ethyl acetate (10 L) four times. The combined organic phase was washed with brine (5 L), dried with anhydrous $Na_2SO_4$, filtered and concentrated in vacuo. The residue was purified by column chromatography (eluting with 0-30% ethyl acetate in petroleum ether) to afford 500 g of (5S)-5-[(1S)-1-hydroxypropyl]tetrahydrofuran-2-one as a yellow oil. (Refer to *Eur. J. Med. Chem.* 1997, 32, 617-623)

Preparation of (5S)-5-[(1S)-1-[tert-butyl(diphenyl)silyl]oxypropyl]tetrahydrofuran-2-one

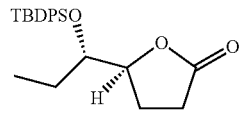

1e

To a mixture of (5S)-5-[(1S)-1-hydroxypropyl]tetrahydrofuran-2-one (500 g, 3.5 mol) and imidazole (708 g, 10.4 mol) in DMF (8.0 L) was added TBDPSCl (1.43 kg, 5.2 mol) dropwise at 0° C. under $N_2$. After being stirred at 25° C. for 12 hours, the reaction mixture was diluted with water (120 mL) and extracted with ethyl acetate (50 mL) three times. The combined organic phase was washed with brine (30 mL), dried over anhydrous $Na_2SO_4$, filtered and concentrated in vacuo. The residue was purified by column chromatography (eluting with 30-50% ethyl acetate in petroleum ether) to afford 860 g of (5S)-5-[(1S)-1-[tert-butyl(diphenyl)silyl]oxypropyl]tetrahydrofuran-2-one as a white solid.

Compound 1e: $^1$H NMR (400 MHz, $CDCl_3$) δ ppm: 0.76 (t, J=7.47 Hz, 3H), 1.08 (s, 9H), 1.36-1.52 (m, 1H), 1.61-1.75 (m, 1H), 2.06-2.24 (m, 2H), 2.41-2.67 (m, 2H), 3.61-3.74 (m, 1H), 4.56 (td, J=7.09, 3.64 Hz, 1H), 7.31-7.57 (m, 6H), 7.61-7.82 (m, 4H).

Preparation of (3S,5S)-5-[(1S)-1-[tert-butyl(diphenyl)silyl]oxypropyl]-3-[(1R)-1-hydroxyethyl]tetrahydrofuran-2-one (Compound 1f-A) and (3S,5S)-5-[(1S)-1-[tert-butyl(diphenyl)silyl]oxypropyl]-3-[(1S)-1-hydroxyethyl]tetrahydrofuran-2-one (Compound 1f-B)

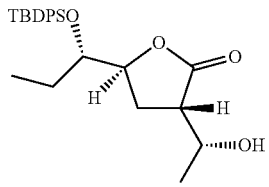

1f-A

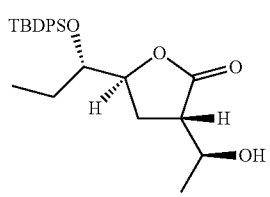

1f-B

To a solution of (5S)-5-[(1S)-1-[tert-butyl(diphenyl)silyl]oxypropyl]tetrahydrofuran-2-one (200 g, 520 mmol) in THF (500 mL) was added LDA (390 mL, 780 mmol) slowly at −78° C. and stirred under $N_2$ for further 2 hours. To the above mixture was added $CH_3CHO$ (34.4 g, 780 mmol) slowly at −78° C. and stirred for another 1 hour. The reaction was quenched with $NH_4Cl$ solution (2 L), diluted with ethyl acetate (2 L), the organic phase was washed with brine (1 L) and dried over anhydrous $Na_2SO_4$, filtered and concentrated in vacuo to give the residue which was purified by column chromatography (eluting with 0-10% ethyl acetate in petroleum ether) twice to give 42 g of (3S,5S)-5-[(1S)-1-[tert-butyl(diphenyl)silyl]oxypropyl]-3-[(1R)-1-hydroxyethyl]tetrahydrofuran-2-one (Compound 1f-A) and 46 g of (3S,5S)-5-[(1S)-1-[tert-butyl(diphenyl)silyl]oxypropyl]-3-[(1S)-1-hydroxyethyl]tetrahydrofuran-2-one (Compound 1f-B).

The stereochemistry on five member ring has been established by 2D NMR NOESY experiments. For Compound 1f-A and Compound 1f-B, correlation of $C^3H$ and $C^5H$ was not observed.

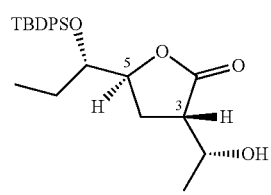

1f-A

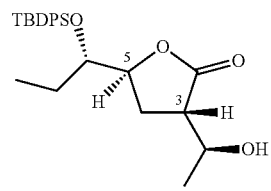

1f-B

Compound 1f-A: $^1$H NMR (400 MHz, $CDCl_3$) δ ppm: 0.72 (t, J=7.53 Hz, 3H), 1.07 (s, 9H), 1.23 (d, J=6.40 Hz, 3H), 1.36-1.51 (m, 1H), 1.65-1.80 (m, 1H), 2.10-2.24 (m, 1H), 2.35 (dt, J=12.83, 9.08 Hz, 1H), 2.86 (ddd, J=10.29, 9.03, 3.14 Hz, 1H), 3.66 (ddd, J=8.28, 5.08, 2.95 Hz, 1H), 4.35 (dd, J=6.40, 3.01 Hz, 1H), 4.58 (dt, J=9.13, 3.15 Hz, 1H), 7.34-7.54 (m, 6H), 7.63-7.81 (m, 4H).

Compound 1f-B: $^1$H NMR (400 MHz, $CDCl_3$) δ ppm: 0.72 (t, J=7.47 Hz, 3H), 1.08 (s, 9H), 1.23 (d, J=6.27 Hz, 3H), 1.38-1.53 (m, 1H), 1.66-1.81 (m, 1H), 1.97 (dt, J=13.05, 9.60 Hz, 1H), 2.24 (ddd, J=12.92, 10.16, 2.51 Hz, 1H), 2.68-2.85 (m, 1H), 3.65 (ddd, J=8.34, 5.08, 2.89 Hz, 1H), 3.79-3.95 (m, 1H), 4.56 (dt, J=9.29, 2.64 Hz, 1H), 7.38-7.54 (m, 6H), 7.70 (ddd, J=10.57, 8.00, 1.51 Hz, 4H).

Preparation of [(1R)-1-[(3S,5S)-5-[(1S)-1-[tert-butyl(diphenyl)silyl]oxypropyl]-2-oxo-tetrahydrofuran-3-yl]ethyl](2S)-3,3,3-trifluoro-2-methoxy-2-phenyl-propanoate (Compound 1p-A) and [(1R)-1-[(3S,5S)-5-[(1S)-1-[tert-butyl(diphenyl)silyl]oxypropyl]-2-oxo-tetrahydrofuran-3-yl]ethyl](2R)-3,3,3-trifluoro-2-methoxy-2-phenyl-propanoate (Compound 1p-B)

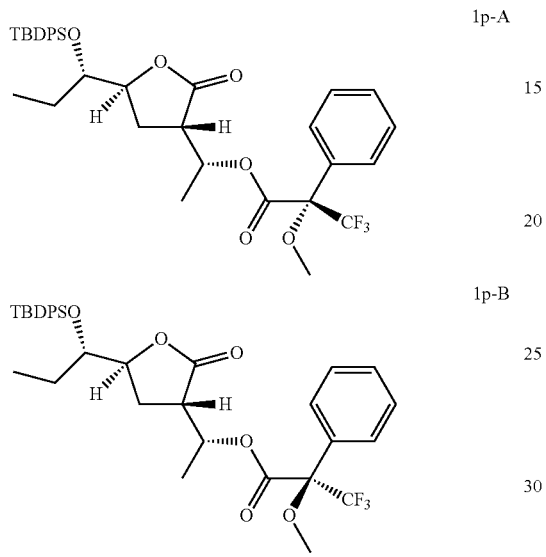

To a solution of (3S,5S)-5-[(1S)-1-[tert-butyl(diphenyl)silyl]oxypropyl]-3-[(1R)-1-hydroxyethyl]tetrahydrofuran-2-one (Compound 1f-A, 20 mg, 0.047 mmol), DMAP (0.6 mg, 0.005 mmol) and Et₃N (9.5 mg, 0.094 mmol) in DCM (2 mL) was added (2R)-3,3,3-trifluoro-2-methoxy-2-phenyl-propanoyl chloride (24 mg, 0.094 mmol) slowly at 0° C. and stirred at 25-28° C. under N₂ for 12 hours. The reaction mixture was quenched with water (3 mL), extracted with DCM (2 mL) twice and dried over anhydrous Na₂SO₄. After concentrated in vacuo, the residue was purified by preparative TLC (eluting with 1:8 ethyl acetate in petroleum ether) to give 10 mg of [(1R)-1-[(3S,5S)-5-[(1S)-1-[tert-butyl(diphenyl)silyl]oxypropyl]-2-oxo-tetrahydrofuran-3-yl]ethyl](2S)-3,3,3-trifluoro-2-methoxy-2-phenyl-propanoate (Compound 1p-A).

In analogy to Compound 1p-A, [(1R)-1-[(3S,5S)-5-[(1S)-1-[tert-butyl(diphenyl)silyl]oxypropyl]-2-oxo-tetrahydrofuran-3-yl]ethyl](2R)-3,3,3-trifluoro-2-methoxy-2-phenyl-propanoate (Compound 1p-B) was prepared by using (2S)-3,3,3-trifluoro-2-methoxy-2-phenyl-propanoyl chloride instead of (2R)-3,3,3-trifluoro-2-methoxy-2-phenyl-propanoyl chloride.

Compound 1p-A: ¹H NMR (400 MHz, CDCl₃) δ ppm: 0.68 (t, J=7.47 Hz, 3H), 1.05 (s, 9H), 1.33-1.41 (m, 1H), 1.43 (d, J=6.40 Hz, 3H), 1.63-1.75 (m, 1H), 2.15-2.24 (m, 2H), 2.97 (td, J=9.63, 3.83 Hz, 1H), 3.50-3.55 (m, 3H), 3.58-3.64 (m, 1H), 4.37-4.45 (m, 1H), 5.54-5.63 (m, 1H), 7.37-7.48 (m, 9H), 7.48-7.54 (m, 2H), 7.63-7.72 (m, 4H).

Compound 1p-B: ¹H NMR (400 MHz, CDCl₃) δ ppm: 0.66 (t, J=7.40 Hz, 3H), 1.05 (s, 9H), 1.34 (d, J=6.27 Hz, 3H), 1.37-1.49 (m, 1H), 1.64-1.75 (m, 1H), 2.13-2.21 (m, 2H), 2.96 (td, J=9.41, 2.64 Hz, 1H), 3.51 (s, 3H), 3.57-3.64 (m, 1H), 4.38-4.49 (m, 1H), 5.50-5.61 (m, 1H), 7.36-7.51 (m, 11H), 7.68 (t, J=8.47 Hz, 4H).

According to the Mosher's model (*Chem. Rev.* 2004, 104, 17-117) and ¹H NMR results, the absolute configurations of Compound 1p-A and Compound 1p-B are shown as above listed. Therefore, the absolute configurations of Compound 1f-A and Compound 1f-B are shown as above.

Preparation of [(3S,5S)-3-[(1R)-1-acetoxyethyl]-5-[(S)-1-[tert-butyl(diphenyl)silyl]oxypropyl]tetrahydrofuran-2-yl] acetate (Compound 1h-A) and [(3S,5S)-3-[(1S)-1-acetoxyethyl]-5-[(1S)-1-[tert-butyl(diphenyl)silyl]oxypropyl]tetrahydrofuran-2-yl] acetate (Compound 1h-B)

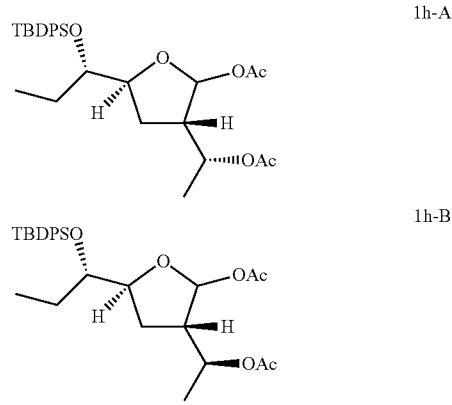

To a solution of (3S,5S)-5-[(1S)-1-[tert-butyl(diphenyl)silyl]oxypropyl]-3-[(1R)-1-hydroxyethyl]tetrahydrofuran-2-one (Compound 1f-A, 17 g, 40 mmol) in toluene (200 mL) was added DIBAL-H (1M, 120 mL, 120 mmol) dropwise at −78° C., and the reaction mixture was stirred at −78° C. under N₂ for 1 hour. The reaction was quenched with saturated NH₄Cl solution and extracted with ethyl acetate. The organic phase was extracted and washed with brine, dried and concentrated to give the crude product, which was re-dissolved in pyridine (100 mL) followed by addition of DMAP (500 mg, 4 mmol) and Ac₂O (30 g, 300 mmol) at 0° C. After being stirred at 25° C. for 16 hours, the reaction was quenched with saturated NaHCO₃ solution and extracted with ethyl acetate. The organic phase was extracted and washed with brine, dried and concentrated to give the crude product, which was purified by column chromatography (eluting with 0-10% ethyl acetate in petroleum ether) to give 13 g of [(3S,5S)-3-[(1R)-1-acetoxyethyl]-5-[(1S)-1-[tert-butyl(diphenyl)silyl]oxypropyl]tetrahydrofuran-2-yl] acetate (Compound 1h-A) as a colorless oil.

In analogy to Compound 1h-A, [(3S,5S)-3-[(1S)-1-acetoxyethyl]-5-[(1S)-1-[tert-butyl(diphenyl)silyl]oxypropyl]tetrahydrofuran-2-yl] acetate (Compound 1h-B) was prepared by using (3S,5S)-5-[(1S)-1-[tert-butyl(diphenyl)silyl]oxypropyl]-3-[(1S)-1-hydroxyethyl]tetrahydrofuran-2-one (Compound 1f-B) instead of Compound 1f-A.

Preparation of [(1R)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl] acetate (Compound 1i-A) and [(1S)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl]acetate (Compound 1i-B)

Preparation of [(1R)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] acetate (Compound 1j-A) and [(1S)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] acetate (Compound 1j-B)

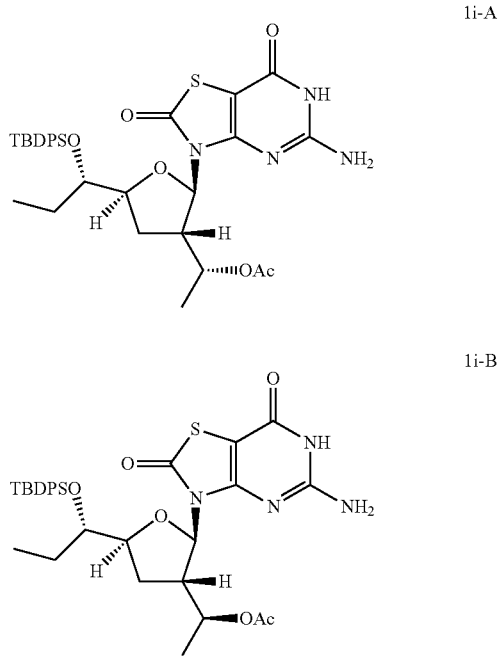

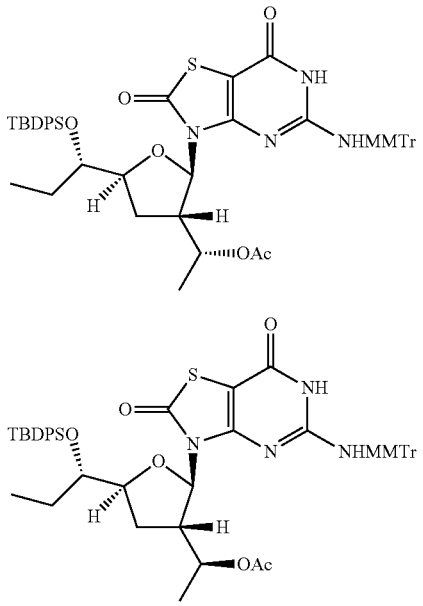

To a suspension of 5-amino-3,6-dihydrothiazolo[4,5-d]pyrimidine-2,7-dione (3.6 g, 20 mmol) in MeCN (100 mL) was added BSA (16 g, 80 mmol) at 25° C., and the reaction mixture was heated to 85° C. for 1 hour until a clear solution was formed. After the mixture was cooled to 0° C., [(3S,5S)-3-[(1R)-1-acetoxyethyl]-5-[(1S)-1-[tert-butyl(diphenyl)silyl]oxypropyl]tetrahydrofuran-2-yl] acetate (Compound 1h-A, 5.2 g, 10 mmol) was added followed by addition of TMSOTf (4.4 g, 20 mmol). After being stirred at 25° C. for 16 hours, the reaction was quenched with saturated NaHCO$_3$ solution and extracted with ethyl acetate. The organic phase was extracted and washed with brine, dried and concentrated in vacuo to give the crude product, which was purified by column chromatography (eluting with 0-2% methanol in DCM) to give 6 g of [(1R)-1-[(2R,3S,5S)-2-(5-amino-2,7-dioxo-6H-thiazolo[4,5-d]pyrimidin-3-yl)-5-[(1 S)-1-[tert-butyl(diphenyl)silyl] oxypropyl]tetrahydrofuran-3-yl]ethyl] acetate (Compound 1i-A) as a yellow foam.

In analogy to Compound 1i-A, [(1S)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl] acetate (Compound 1i-B) was prepared by using [(3S,5S)-3-[(1S)-1-acetoxyethyl]-5-[(1S)-1-[tert-butyl(diphenyl)silyl]oxypropyl]tetrahydrofuran-2-yl] acetate (Compound 1h-B) instead of Compound 1h-A.

To a solution of [(1R)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl] acetate (Compound 1i-A, 3.7 g, 5.8 mmol) in DCM (100 mL) was added collidine (2.1 g, 17.4 mmol), AgNO$_3$ (2.9 g, 17.4 mmol) and MMTrCl (5.4 g, 17.4 mmol) at 0° C., and the reaction mixture was stirred at 20° C. for 2 hours. Then the reaction was quenched with water (80 mL), and the reaction mixture was filtered and extracted with ethyl acetate (100 mL) three times. The combined organic layer was dried over anhydrous Na$_2$SO$_4$, filtered, concentrated, and the residue was purified by column chromatography (eluting with 1-5% methanol in DCM) to give 5.0 g of [(1R)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl]acetate (Compound 1j-A) as a yellow solid. MS obsd. (ESI$^+$) [(M+H)$^+$]: 909.3.

In analogy to Compound 1j-A, [(1S)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] acetate (Compound 1j-B) was prepared by using [(1S)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl] acetate (Compound 1i-B) instead of Compound 1i-A.

Preparation of 3-[(2R,3S,5S)-5-[(S)-1-[tert-butyl(diphenyl)silyl]oxypropyl]-3-[(1R)-1-hydroxyethyl]tetrahydrofuran-2-yl]-5-[[(4-methoxyphenyl)-diphenyl-methyl]amino]-6H-thiazolo[4,5-d]pyrimidine-2,7-dione (Compound 1k-A) and 3-[(2R,3S,5S)-5-[(1S)-1-[tert-butyl(diphenyl)silyl]oxypropyl]-3-[(S)-1-hydroxyethyl]tetrahydrofuran-2-yl]-5-[[(4-methoxyphenyl)-diphenyl-methyl]amino]-6H-thiazolo[4,5-d]pyrimidine-2,7-dione (Compound 1k-B)

Preparation of [(1R)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] methanesulfonate (Compound 1l-A) and [(1S)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] methanesulfonate (Compound 1l-B)

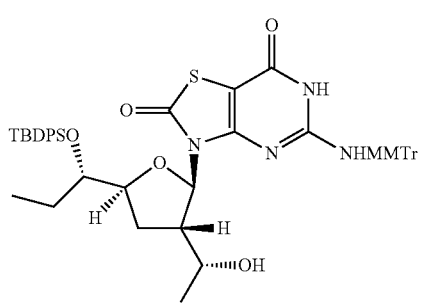

1k-A

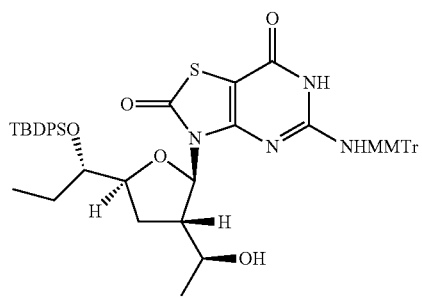

1k-B

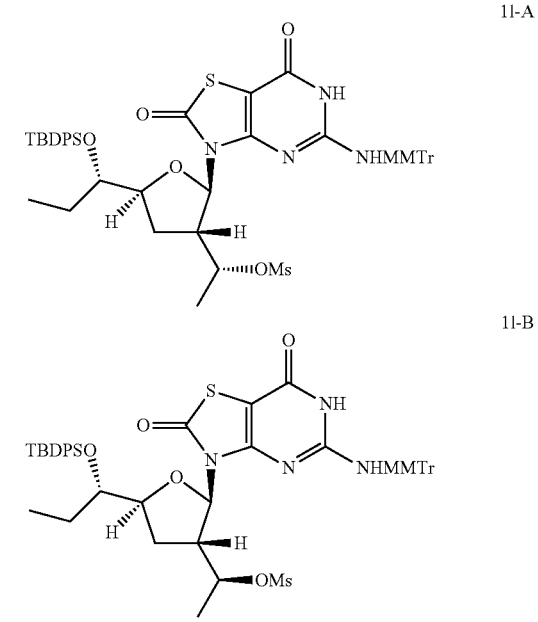

To a solution of [(1R)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] acetate (Compound 1j-A, 5.0 g, 5.5 mmol) in methanol (60.0 mL) was added $K_2CO_3$ (4.5 g, 33.0 mmol). The mixture was stirred at 25° C. for 12 hours. The solid was removed by filtration and the filtrate was concentrated in vacuo. Then the residue was purified by column chromatography (eluting with 2-5% methanol in DCM) to give 3.8 g of 3-[(2R,3S,5S)-5-[(1S)-1-[tert-butyl(diphenyl)silyl]oxypropyl]-3-[(1R)-1-hydroxyethyl]tetrahydrofuran-2-yl]-5-[[(4-methoxyphenyl)-diphenyl-methyl]amino]-6H-thiazolo[4,5-d]pyrimidine-2,7-dione (Compound 1k-A) as a white solid.

In analogy to Compound 1k-A, 3-[(2R,3S,5S)-5-[(1S)-1-[tert-butyl(diphenyl)silyl]oxypropyl]-3-[(1S)-1-hydroxyethyl]tetrahydrofuran-2-yl]-5-[[(4-methoxyphenyl)-diphenyl-methyl]amino]-6H-thiazolo[4,5-d]pyrimidine-2,7-dione (Compound 1k-B) was prepared by using [(1S)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] acetate (Compound 1j-B) instead of Compound 1j-A.

To a solution of 3-[(2R,3S,5S)-5-[(1S)-1-[tert-butyl(diphenyl)silyl]oxypropyl]-3-[(1S)-1-hydroxyethyl]tetrahydrofuran-2-yl]-5-[[(4-methoxyphenyl)-diphenyl-methyl]amino]-6H-thiazolo[4,5-d]pyrimidine-2,7-dione (Compound 1k-B, 2.5 g, 2.88 mmol) in pyridine (20.0 mL) was added methanesulfonyl chloride (495.4 mg, 4.32 mmol) dropwise at 0° C. and the reaction mixture was stirred at 25° C. under $N_2$ for 12 hours. The reaction was quenched with aqueous $NaHCO_3$ (50 mL), extracted with ethyl acetate (50 mL) twice, the combined organic layer was dried over anhydrous $Na_2SO_4$. After filtration, the solvent was removed in vacuo to give 2.5 g of the crude [(1S)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] methanesulfonate (Compound 1l-B) as a brown oil, which was used in the next step directly without further purification.

In analogy to Compound 1l-B, [(1R)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] methanesulfonate (Compound 1l-A) was prepared by using 3-[(2R,3S,5S)-5-[(1S)-1-[tert-butyl(diphenyl)silyl]oxypropyl]-3-[(1R)-1-hydroxyethyl]tetrahydrofuran-2-yl]-5-[[(4-methoxyphenyl)-diphenyl-methyl]amino]-6H-thiazolo[4,5-d]pyrimidine-2,7-dione (Compound 1k-A) instead of Compound 1k-B.

Preparation of 3-[(2R,3S,5S)-3-[(1S)-1-azidoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1m-A) and 3-[(2R,3S,5S)-3-[(1R)-1-azidoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1m-B)

Preparation of 3-[(2R,3S,5S)-3-[(1S)-1-aminoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1n-A) and 3-[(2R,3S,5S)-3-[(1R)-1-aminoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1n-B)

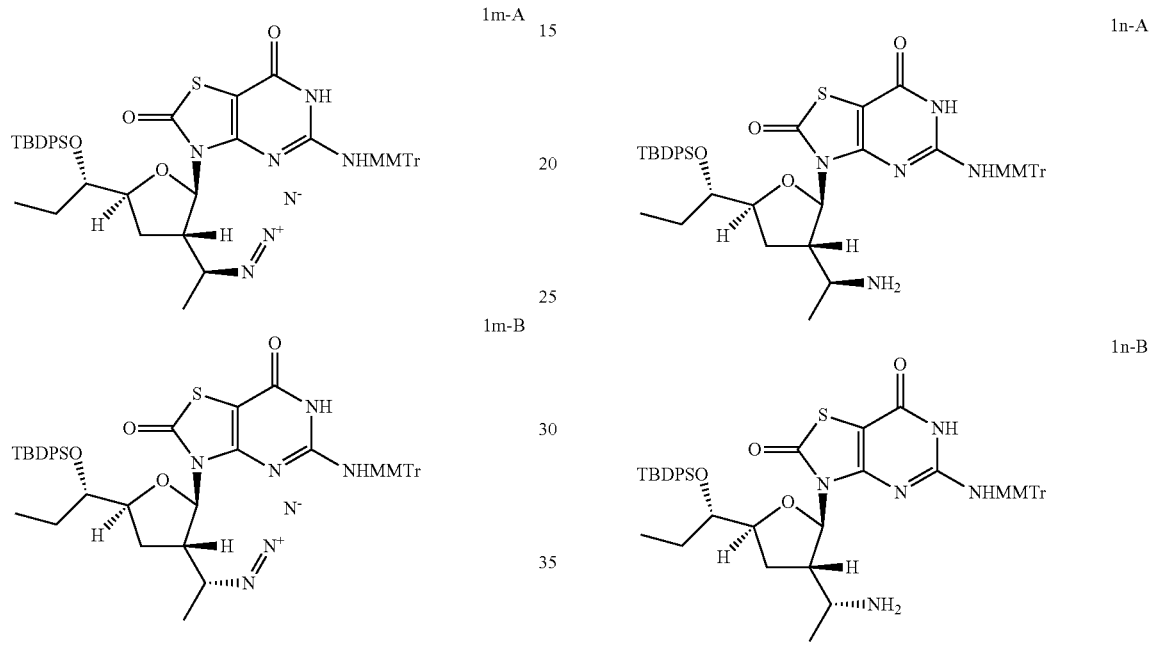

To a solution of [(1S)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] methanesulfonate (Compound 1l-B, 1.3 g, 1.38 mmol) in N,N-dimethylformamide (10.0 mL) was added sodium azide (268.2 mg, 4.13 mmol) slowly at 25° C. and the reaction mixture was stirred at 60-80° C. under $N_2$ for 12 hours. The reaction solution was cooled to 25° C. and poured into water (50.0 mL), extracted with ethyl acetate (30 mL) twice. The combined organic layer was dried over anhydrous $Na_2SO_4$. After filtration, the solvent was removed in vacuo and the residue was purified by column chromatography (eluting with 0-2% methanol in DCM) to give 0.75 g of 3-[(2R,3S,5S)-3-[(1R)-1-azidoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1m-B) as a brown solid.

In analogy to Compound 1m-B, 3-[(2R,3S,5S)-3-[(1S)-1-azidoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1m-A) was prepared by using [(1R)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] methanesulfonate (Compound 1l-A) instead of Compound 1l-B.

To a solution of 3-[(2R,3S,5S)-3-[(1R)-1-azidoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1m-B, 2.1 g, 2.35 mmol) in tetrahydrofuran (20.0 mL) was added Zn (307.8 mg, 4.7 mmol) and acetic acid (282.7 mg, 4.7 mmol), then the reaction mixture was stirred at 25° C. for 12 hours. The reaction was quenched with saturate $NaHCO_3$ (10 mL) solution and extracted with ethyl acetate (30 mL) twice. The organic layer was dried over anhydrous $Na_2SO_4$ and concentrated in vacuo. The residue was purified by column chromatography (eluting with 0-2% methanol in DCM) to give 1.4 g of 3-[(2R,3S,5S)-3-[(1R)-1-aminoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1n-B) as a yellow solid.

In analogy to Compound 1n-B, 3-[(2R,3S,5S)-3-[(1S)-1-aminoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1n-A) was prepared by using 3-[(2R,3S,5S)-3-[(1S)-1-azidoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1m-A) instead of Compound 1m-B.

Preparation of 3-[(2R,3S,5S)-3-[(1S)-1-aminoethyl]-5-[(1S)-1-hydroxypropyl]tetrahydrofuran-2-yl]-5-[[(4-methoxyphenyl)-diphenyl-methyl]amino]-6H-thiazolo[4,5-d]pyrimidine-2,7-dione (Compound 1o-A) and 3-[(2R,3S,5S)-3-[(1R)-1-aminoethyl]-5-[(1S)-1-hydroxypropyl]tetrahydrofuran-2-yl]-5-[[(4-methoxyphenyl)-diphenyl-methyl]amino]-6H-thiazolo[4,5-d]pyrimidine-2,7-dione (Compound 1o-B)

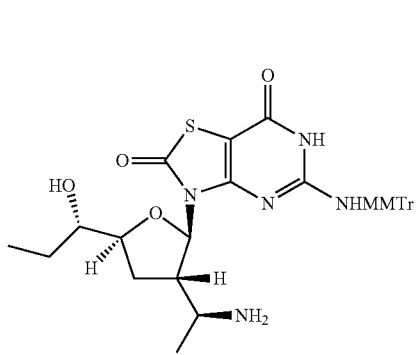

1o-A

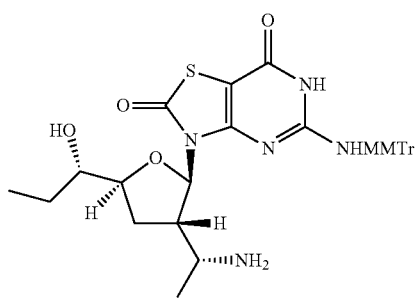

1o-B

A solution of 3-[(2R,3S,5S)-3-[(1R)-1-aminoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1n-B, 0.32 g, 0.36 mmol) in tetrabutylammonium fluoride (3M in THF, 10.0 mL) was stirred at 50° C. for 12 hours. The reaction solution was diluted with water (20 mL), extracted with ethyl acetate (20 mL) twice. The combined organic layer was dried over anhydrous Na$_2$SO$_4$, filtered and concentrated in vacuo. The residue was purified by column chromatography (eluting with 10-30% ethyl acetate in petroleum ether) to give 0.21 g of 3-[(2R,3S,5S)-3-[(1R)-1-aminoethyl]-5-[(1S)-1-hydroxypropyl]tetrahydrofuran-2-yl]-5-[[(4-methoxyphenyl)-diphenyl-methyl]amino]-6H-thiazolo[4,5-d]pyrimidine-2,7-dione (Compound 1o-B) as a yellow solid.

In analogy to Compound 1o-B, 3-[(2R,3S,5S)-3-[(1S)-1-aminoethyl]-5-[(1S)-1-hydroxypropyl]tetrahydrofuran-2-yl]-5-[[(4-methoxyphenyl)-diphenyl-methyl]amino]-6H-thiazolo[4,5-d]pyrimidine-2,7-dione (Compound 1o-A) was prepared by using 3-[(2R,3S,5S)-3-[(1S)-1-aminoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1n-A) instead of Compound 1n-B.

Preparation of 5-amino-3-[(2R,3S,5S)-3-[(1S)-1-aminoethyl]-5-[(1S)-1-hydroxypropyl]tetrahydrofuran-2-yl]-6H-thiazolo[4,5-d]pyrimidine-2,7-dione (Example 1-A) and 5-amino-3-[(2R,3S,5S)-3-[(1R)-1-aminoethyl]-5-[(1S)-1-hydroxypropyl]tetrahydrofuran-2-yl]-6H-thiazolo[4,5-d]pyrimidine-2,7-dione (Example 1-B)

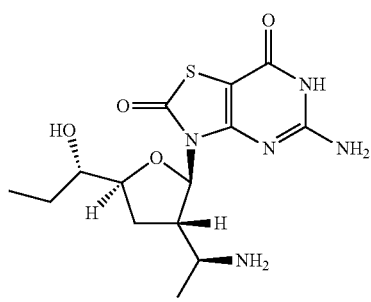

1-A

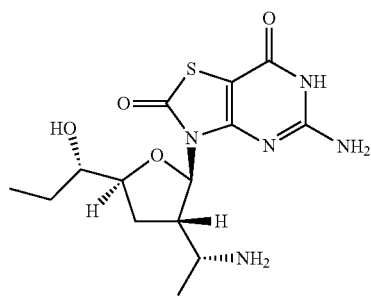

1-B

A solution of 3-[(2R,3S,5S)-3-[(1R)-1-aminoethyl]-5-[(1S)-1-hydroxypropyl]tetrahydrofuran-2-yl]-5-[[(4-methoxyphenyl)-diphenyl-methyl]amino]-6H-thiazolo[4,5-d]pyrimidine-2,7-dione (Compound 1o-B, 200.0 mg, 0.49 mmol) in formic acid (5.0 mL) was stirred at 20-25° C. under N$_2$ for 0.5 hour. The mixture was concentrated in vacuo and the residue was purified by preparative HPLC and SFC to give 23.0 mg of 5-amino-3-[(2R,3S,5S)-3-[(1R)-1-aminoethyl]-5-[(1S)-1-hydroxypropyl]tetrahydrofuran-2-yl]-6H-thiazolo[4,5-d]pyrimidine-2,7-dione (Example 1-B) as a light yellow solid.

In analogy to Example 1-B, 5-amino-3-[(2R,3S,5S)-3-[(1S)-1-aminoethyl]-5-[(1S)-1-hydroxypropyl]tetrahydrofuran-2-yl]-6H-thiazolo[4,5-d]pyrimidine-2,7-dione (Example 1-A) was prepared by using 3-[(2R,3S,5S)-3-[(1S)-1-aminoethyl]-5-[(1S)-1-hydroxypropyl]tetrahydrofuran-2-yl]-5-[[(4-methoxyphenyl)-diphenyl-methyl]amino]-6H-thiazolo[4,5-d]pyrimidine-2,7-dione (Compound 1o-A) instead of Compound 1o-B.

Example 1-A: MS obsd. (ESI$^+$) [(M+H)$^+$]: 356.1; $^1$H NMR (400 MHz, DMSO-d$_6$) δ ppm: 1.01 (t, J=7.40 Hz, 3H), 1.19 (d, J=6.40 Hz, 3H), 1.43-1.63 (m, 2H), 1.94-2.09 (m, 1H), 2.35 (ddd, J=12.64, 9.69, 6.02 Hz, 1H), 2.91-3.02 (m, 1H), 3.10 (quin, J=6.74 Hz, 1H), 3.48 (dt, J=8.50, 4.34 Hz, 1H), 4.03-4.15 (m, 1H), 6.07 (d, J=6.78 Hz, 1H).

Example 1-B: MS obsd. (ESI$^+$) [(M+H)$^+$]: 356.1; $^1$H NMR (400 MHz, DMSO-d$_6$) δ ppm: 0.89 (t, J=7.34 Hz, 3H) 0.97 (d, J=6.27 Hz, 3H), 1.21-1.36 (m, 1H), 1.37-1.56 (m, 1H), 1.89-2.01 (m, 1H), 2.09-2.21 (m, 1H), 2.82 (br. s., 1H), 2.87-2.98 (m, 1H), 3.80-3.90 (m, 1H), 4.71 (br. s., 1H), 5.83 (d, J=5.77 Hz, 1H), 7.09 (br. s., 2H).

Example 2

5-Amino-3-[(2R,3S,5S)-5-[(1S)-1-hydroxypropyl]-3-[(1R)-1-(methylamino)ethyl]tetrahydrofuran-2-yl]-6H-thiazolo[4,5-d]pyrimidine-2,7-dione

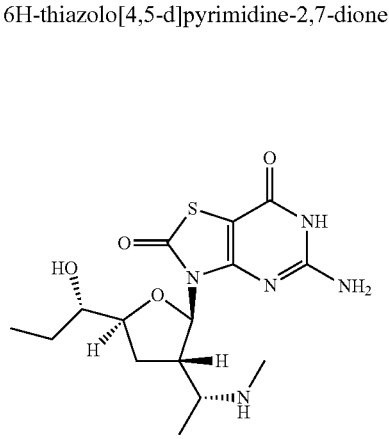

Preparation of 3-[(2R,3S,5S)-5-[(1S)-1-[tert-butyl(diphenyl)silyl]oxypropyl]-3-[(1R)-1-(methylamino)ethyl]tetrahydrofuran-2-yl]-5-[[(4-methoxyphenyl)-diphenyl-methyl]amino]-6H-thiazolo[4,5-d]pyrimidine-2,7-dione (Compound 2a)

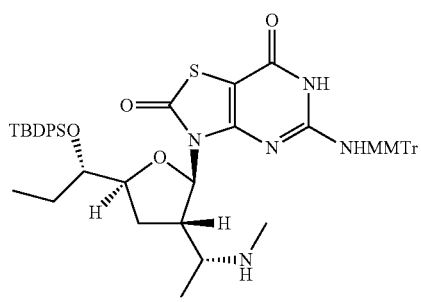

[(1S)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl]methanesulfonate (Compound 11-B, 1.8 g, 1.9 mmol) was dissolved in a solution of MeNH₂ in ethanol (33 wt. % in absolute ethanol, 20.0 mL, 149 mmol) and the reaction mixture was heated with stirring at 80° C. under N₂ for 20 hours. The reaction solution was cooled to 25° C. and concentrated in vacuo, and the residue was purified by column chromatography (eluting with 0-2% methanol in DCM) to give 0.8 g of 3-[(2R,3S,5S)-5-[(1S)-1-[tert-butyl(diphenyl)silyl]oxypropyl]-3-[(1R)-1-(methylamino)ethyl]tetrahydrofuran-2-yl]-5-[[(4-methoxyphenyl)-diphenyl-methyl]amino]-6H-thiazolo[4,5-d]pyrimidine-2,7-dione (Compound 2a) as a yellow solid.

Preparation of 3-[(2R,3S,5S)-5-[(1S)-1-hydroxypropyl]-3-[(1R)-1-(methylamino)ethyl]tetrahydrofuran-2-yl]-5-[[(4-methoxyphenyl)-diphenyl-methyl]amino]-6H-thiazolo[4,5-d]pyrimidine-2,7-dione (Compound 2b)

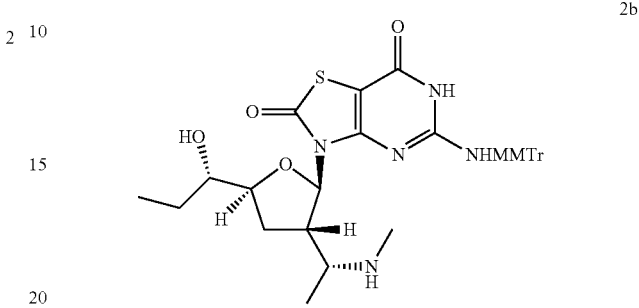

A solution of 3-[(2R,3S,5S)-5-[(1S)-1-[tert-butyl(diphenyl)silyl]oxypropyl]-3-[(1R)-1-(methylamino)ethyl]tetrahydrofuran-2-yl]-5-[[(4-methoxyphenyl)-diphenyl-methyl]amino]-6H-thiazolo[4,5-d]pyrimidine-2,7-dione (Compound 2a, 1.7 g, 2.0 mmol) in tetrabutylammonium fluoride (1M in THF, 10.0 mL, 10.0 mmol) was stirred at 50° C. for 16 hours. The reaction solution was diluted with water (50.0 mL), extracted with DCM/methanol (10:1, 100 mL) twice. The combined organic layer was dried over anhydrous Na₂SO₄, filtered and concentrated in vacuo. The residue was purified by column chromatography (eluting with 0-5% methanol in DCM) to give 1.0 g of 3-[(2R,3S,5S)-5-[(1S)-1-hydroxypropyl]-3-[(1R)-1-(methylamino)ethyl]tetrahydrofuran-2-yl]-5-[[(4-methoxyphenyl)-diphenyl-methyl]amino]-6H-thiazolo[4,5-d]pyrimidine-2,7-dione (Compound 2b) as a yellow oil.

Preparation of 5-amino-3-[(2R,3S,5S)-5-[(1S)-1-hydroxypropyl]-3-[(1R)-1-(methylamino)ethyl]tetrahydrofuran-2-yl]-6H-thiazolo[4,5-d]pyrimidine-2,7-dione (Example 2)

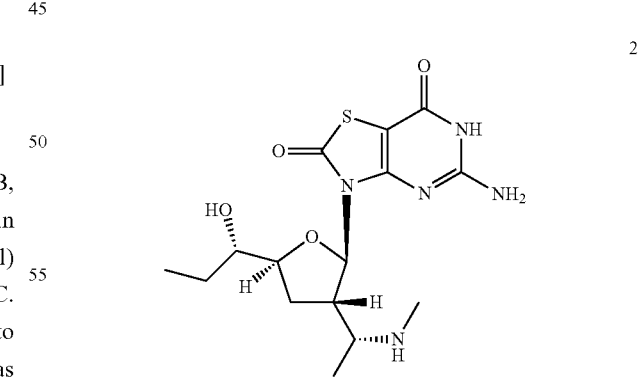

A solution of 3-[(2R,3S,5S)-5-[(1S)-1-hydroxypropyl]-3-[(1R)-1-(methylamino)ethyl]tetrahydrofuran-2-yl]-5-[[(4-methoxyphenyl)-diphenyl-methyl]amino]-6H-thiazolo[4,5-d]pyrimidine-2,7-dione (Compound 2b, 1.0 g, 1.5 mmol) in formic acid (10.0 mL) was stirred at 20-25° C. under N₂ for 20 minutes. The mixture was concentrated under reduced pressure and the residue was purified by preparative HPLC to give 0.12 g of 5-amino-3-[(2R,3S,5S)-5-[(1S)-1-hydroxy-propyl]-3-[(1R)-1-(methylamino)ethyl]tetrahydrofuran-2-yl]-6H-thiazolo[4,5-d]pyrimidine-2,7-dione (Example 2) as a white solid.

Example 2: MS obsd. (ESI⁺) [(M+H)⁺]: 370.0; $^1$H NMR (400 MHz, Methanol-$d_4$) δ ppm: 1.001 (t, J=7.40 Hz, 3H), 1.09 (d, J=6.53 Hz, 3H), 1.42-1.64 (m, 2H), 2.06 (dt, J=12.52, 7.92 Hz, 1H), 2.37-2.43 (m, 1H), 2.44 (s, 3H), 2.74-2.87 (m, 1H), 3.13-3.24 (m, 1H), 3.47 (dt, J=8.50, 4.34 Hz, 1H), 4.03-4.14 (m, 1H), 6.03 (d, J=7.15 Hz, 1H).

Example 3

5-Amino-3-[(2R,3S,5S)-5-[(1S)-1-hydroxypropyl]-3-[(1R)-1-(propylamino)ethyl]tetrahydrofuran-2-yl]-6H-thiazolo[4,5-d]pyrimidine-2,7-dione

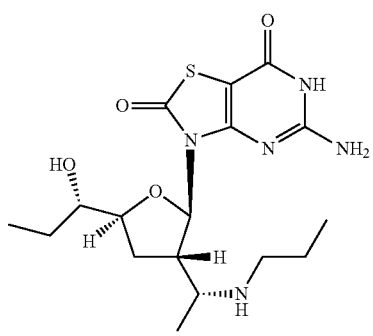

3

The title compound was prepared in analogy to Example 2, by using propylamine instead of methylamine. The final product was purified by preparative HPLC and SFC to afford Example 3 as a white solid.

Example 3: MS obsd. (ESI⁺) [(M+H)⁺]: 398.1; $^1$H NMR (400 MHz, Methanol-$d_4$) δ ppm: 0.95 (t, J=7.40 Hz, 3H), 1.01 (t, J=7.40 Hz, 3H), 1.13 (d, J=6.4, 3H), 1.33-1.61 (m, 4H), 2.05 (dt, J=12.36, 7.87 Hz, 1H), 2.42 (ddd, J=12.55, 9.60, 6.09 Hz, 1H), 2.58 (ddd, J=11.45, 8.56, 6.46 Hz, 1H), 2.67-2.77 (m, 1H), 2.94 (quin, J=6.74 Hz, 1H), 3.17-3.28 (m, 1H), 3.49 (dt, J=8.53, 4.39 Hz, 1H), 4.03-4.14 (m, 1H), 6.05 (d, J=6.90 Hz, 1H).

Example 4

5-Amino-3-[(2R,3S,5S)-3-[(1R)-1-(cyclopropy-lamino)ethyl]-5-[(1S)-1-hydroxypropyl]tetrahydro-furan-2-yl]-6H-thiazolo[4,5-d]pyrimidine-2,7-dione

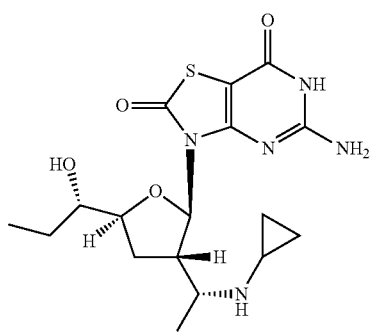

4

The title compound was prepared in analogy to Example 2, by using cyclopropylamine instead of methylamine. The final product was purified by preparative HPLC and SFC to afford Example 4 as a white solid.

Example 4: MS obsd. (ESI⁺) [(M+H)⁺]: 396.1; $^1$H NMR (400 MHz, Methanol-$d_4$) δ ppm: 0.51-0.86 (m, 4H), 1.01 (t, J=7.40 Hz, 3H), 1.28 (d, J=6.02 Hz, 3H), 1.40-1.69 (m, 2H), 1.98-2.15 (m, 1H), 2.31-2.57 (m, 2H), 3.25-3.37 (m, 2H), 3.49 (dt, J=8.66, 4.33 Hz, 1H), 3.97-4.16 (m, 1H), 6.06 (d, J=6.27 Hz, 1H).

Example 5

5-Amino-3-[(2R,3S,5S)-3-[(1R)-1-(benzylamino)ethyl]-5-[(1S)-1-hydroxypropyl]tetrahydrofuran-2-yl]-6H-thiazolo[4,5-d]pyrimidine-2,7-dione

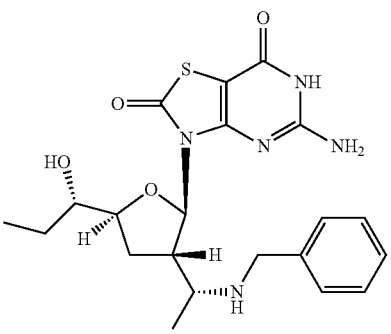

5

The title compound was prepared in analogy to Example 2, by using benzylamine instead of methylamine. The final product was purified by preparative HPLC and SFC to afford Example 5 as a light yellow solid.

Example 5: MS obsd. (ESI⁺) [(M+H)⁺]: 446.1; $^1$H NMR (400 MHz, Methanol-$d_4$) δ ppm: 0.99 (t, J=7.40 Hz, 3H), 1.14 (d, J=6.40 Hz, 3H), 1.38-1.64 (m, 2H), 1.87-2.09 (m, 1H), 2.38 (ddd, J=12.30, 9.47, 6.71 Hz, 1H), 2.86 (t, J=6.15 Hz, 1H), 3.14-3.27 (m, 1H), 3.47 (dt, J=8.53, 4.39 Hz, 1H), 3.73 (d, J=13.05 Hz, 1H), 3.91 (d, J=13.18 Hz, 1H), 3.98-4.07 (m, 1H), 6.07 (d, J=6.53 Hz, 1H), 7.16-7.41 (m, 5H).

Example 6

5-Amino-3-[(2R,3S,5S)-5-[(1S)-1-hydroxypropyl]-3-[(1S)-1-(methylamino)ethyl]tetrahydrofuran-2-yl]-6H-thiazolo[4,5-d]pyrimidine-2,7-dione

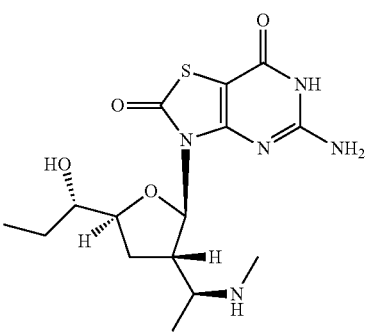

6

The title compound was prepared in analogy to Example 2, by using Compound 1l-A instead of Compound 1l-B. The final product was purified by preparative HPLC to afford Example 6 as a white solid.
Example 6: MS obsd. (ESI+) [(M+H)+]: 370.0; ¹H NMR (400 MHz, Methanol-d₄) δ ppm: 1.01 (t, J=7.47 Hz, 3H), 1.16 (d, J=6.53 Hz, 3H), 1.45-1.62 (m, 2H), 2.06 (dt, J=12.58, 8.20 Hz, 1H), 2.24-2.31 (m, 1H), 2.34 (s, 3H), 2.77 (quin, J=6.40 Hz, 1H), 3.17 (dt, J=15.47, 7.64 Hz, 1H), 3.41-3.53 (m, 1H), 4.01-4.16 (m, 1H), 6.04 (d, J=7.28 Hz, 1H).

Example 7

5-Amino-3-[(2R,3S,5S)-3-[(1S)-1-(benzylamino) ethyl]-5-[(1S)-1-hydroxypropyl]tetrahydrofuran-2-yl]-6H-thiazolo[4,5-d]pyrimidine-2,7-dione

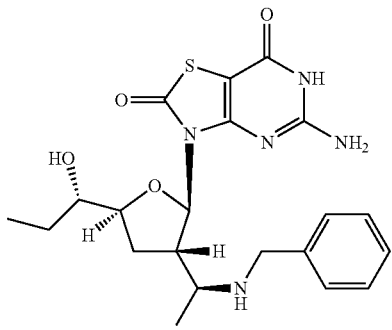

7

The title compound was prepared in analogy to Example 5, by using Compound 1l-A instead of Compound 1l-B. The final product was purified by preparative HPLC to afford Example 7 as a light yellow solid.
Example 5: MS obsd. (ESI+) [(M+H)+]: 446.0; ¹H NMR (400 MHz, Methanol-d₄) δ ppm: 1.01 (t, J=7.47 Hz, 3H), 1.40 (d, J=6.53 Hz, 3H), 1.45-1.64 (m, 2H), 2.09-2.20 (m, 1H), 2.23-2.33 (m, 1H), 3.20 (m, 1H), 3.36-3.43 (m, 1H), 3.48 (dt, J=8.31, 4.31 Hz, 1H), 4.01 (d, J=13.2, 1H), 4.11 (d, J=13.2, 1H), 4.10-4.18 (m, 1H), 6.03 (d, J=7.40 Hz, 1H), 7.37 (s, 5H).

Example 8

5-Amino-3-[(2R,3S,5S)-3-[(1R)-1-(dimethylamino) ethyl]-5-[(1S)-1-hydroxypropyl]tetrahydrofuran-2-yl]-6H-thiazolo[4,5-d]pyrimidine-2,7-dione

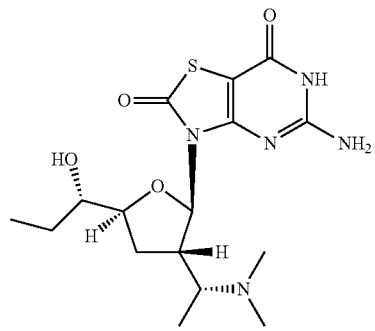

8

Preparation of 3-[(2R,3S,5S)-5-[(1S)-1-[tert-butyl (diphenyl)silyl]oxypropyl]-3-[(1R)-1-(dimethyl-amino)ethyl]tetrahydrofuran-2-yl]-5-[[(4-methoxy-phenyl)-diphenyl-methyl]amino]-6H-thiazolo[4,5-d] pyrimidine-2,7-dione (Compound 8a)

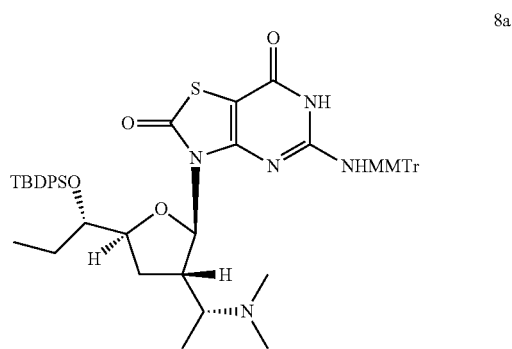

8a

To a solution of 3-[(2R,3S,5S)-3-[(1R)-1-aminoethyl]-5-[(1S)-1-[tert-butyl(diphenyl)silyl]oxypropyl]tetrahydrofuran-2-yl]-5-[[(4-methoxyphenyl)-diphenyl-methyl]amino]-6H-thiazolo[4,5-d]pyrimidine-2,7-dione (Compound 1n-B, 400.0 mg, 0.46 mmol) in dichloroethane (20.0 mL) was added s-trioxane (208.0 mg, 2.3 mmol) and acetic acid (30.0 mg, 0.456 mmol). After the reaction mixture was stirred at 25° C. for 0.5 hour, NaBH(OAc)₃ (293.6 mg, 1.4 mmol) was added. After addition, the reaction mixture was stirred at 25° C. for another 12 hours, and then filtered and the filtrate was concentrated in vacuo. The residue was purified by column chromatography (eluting with 10-30% ethyl acetate in petroleum ether, and then 1% methanol in DCM) to give 400.0 mg of 3-[(2R,3S,5S)-5-[(1S)-1-[tert-butyl(diphenyl)silyl] oxypropyl]-3-[(1R)-1-(dimethylamino)ethyl]tetrahydrofuran-2-yl]-5-[[(4-methoxyphenyl)-diphenyl-methyl]amino]-6H-thiazolo[4,5-d]pyrimidine-2,7-dione (Compound 8a) as a yellow solid.

Preparation of 3-[(2R,3S,5S)-3-[(1R)-1-(dimethyl-amino)ethyl]-5-[(1S)-1-hydroxypropyl]tetrahydro-furan-2-yl]-5-[[(4-methoxyphenyl)-diphenyl-methyl] amino]-6H-thiazolo[4,5-d]pyrimidine-2,7-dione (Compound 8b)

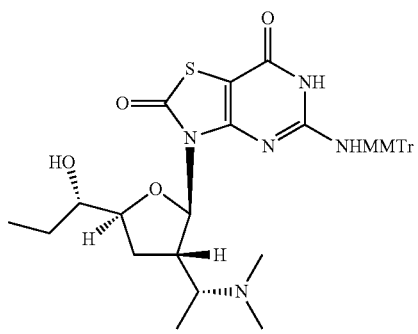

8b

A solution of 3-[(2R,3S,5S)-5-[(1S)-1-[tert-butyl(diphenyl)silyl]oxypropyl]-3-[(1R)-1-(dimethylamino)ethyl]tetrahydrofuran-2-yl]-5-[[(4-methoxyphenyl)-diphenyl-methyl]

amino]-6H-thiazolo[4,5-d]pyrimidine-2,7-dione (Compound 8a, 0.4 g, 0.46 mmol) in tetrabutylammonium fluoride (3M in THF, 10.0 mL) was stirred at 50° C. for 12 hours. The reaction solution was diluted with water (20.0 mL), extracted with ethyl acetate (20 mL) twice. The combined organic layer was dried over anhydrous Na$_2$SO$_4$, filtered and concentrated under reduced pressure. The residue was purified by column chromatography (eluting with 10-30% ethyl acetate in petroleum ether) to give 210.0 mg of 3-[(2R,3S,5S)-3-[(1R)-1-(dimethylamino)ethyl]-5-[(1S)-1-hydroxypropyl]tetrahydrofuran-2-yl]-5-[[(4-methoxyphenyl)-diphenyl-methyl]amino]-6H-thiazolo[4,5-d]pyrimidine-2,7-dione (Compound 8b) as a yellow solid.

Preparation of 5-amino-3-[(2R,3S,5S)-3-[(1R)-1-(dimethylamino)ethyl]-5-[(1S)-1-hydroxypropyl]tetrahydrofuran-2-yl]-6H-thiazolo[4,5-d]pyrimidine-2,7-dione (Example 8)

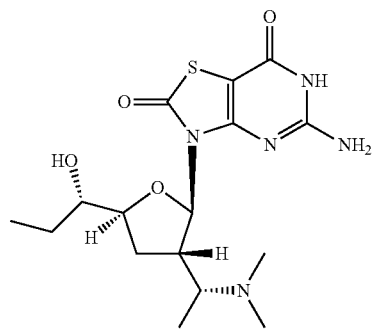

8

A solution of 3-[(2R,3S,5S)-3-[(1R)-1-(dimethylamino)ethyl]-5-[(1S)-1-hydroxypropyl]tetrahydrofuran-2-yl]-5-[[(4-methoxyphenyl)-diphenyl-methyl]amino]-6H-thiazolo[4,5-d]pyrimidine-2,7-dione (Compound 8b, 200 mg, 0.49 mmol) in formic acid (5.0 mL) was stirred at 20-25° C. under N$_2$ for 30 minutes. The mixture was concentrated in vacuo and the residue was purified by preparative HPLC to give 25.2 mg of 5-amino-3-[(2R,3S,5S)-3-[(1R)-1-(dimethylamino)ethyl]-5-[(1S)-1-hydroxypropyl]tetrahydrofuran-2-yl]-6H-thiazolo[4,5-d]pyrimidine-2,7-dione (Example 8) as a light yellow solid.
Example 8: MS obsd. (ESI$^+$) [(M+H)$^+$]: 384.1; $^1$H NMR (400 MHz, Methanol-d$_4$) δ ppm: 0.87 (d, J=6.40 Hz, 3H), 1.00 (t, J=7.59 Hz, 3H), 1.51 (m, 2H), 2.22 (m, 7H), 2.31-2.41 (m, 1H), 2.67 (m., 1H), 3.17-3.25 (m, 1H), 3.48 (m, 1H), 4.02 (m, 1H), 5.95 (d, J=7.15 Hz, 1H).

Example 9

HEK293-Blue-hTLR-7 Cells Assay
A stable HEK293-Blue-hTLR-7 cell line was purchased from InvivoGen (Cat. #: hkb-htlr7, San Diego, Calif., USA). These cells were designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was regulated by the NF-κB promoter upon stimulation of human TLR7. The cell culture supernatant SEAP reporter activity was determined using QUANTI-Blue™ kit (Cat. #: rep-qb 1, Invivogen, San Diego, Calif., USA) at a wavelength of 640 nm, a detection medium that turns purple to blue in the presence of alkaline phosphatase.

HEK293-Blue-hTLR7 cells were incubated at a density of 250,000~450,000 cells/mL in a volume of 180 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum for 24 hours. Then the HEK293-Blue-hTLR-7 cells were incubated with addition of 20 μL test compound in a serial dilution in the presence of final DMSO at 1% and perform incubation under 37° C. in a CO$_2$ incubator for 20 hours. Then 20 μL of the supernatant from each well was incubated with 180 μL Quanti-blue substrate solution at 37° C. for 1-3 hours and the absorbance was read at 620-655 nm using a spectrophotometer. The signalling pathway that TLR7 activation leads to downstream NF-κB activation has been widely accepted, and therefore similar reporter assay was also widely used for evaluating TLR7 agonist (Tsuneyasu Kaisho and Takashi Tanaka, Trends in Immunology, Volume 29, Issue 7, July 2008, Pages 329. sci; Hiroaki Hemmi et al, Nature Immunology 3, 2002, 196-200).

HEK293-Blue-hTLR-8 cells assay:
A stable HEK293-Blue-hTLR-8 cell line was purchased from InvivoGen (Cat. #: hkb-htlr8, San Diego, Calif., USA). These cells were designed for studying the stimulation of human TLR8 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR8 cells with TLR8 ligands. Therefore the reporter expression was regulated by the NF-κB promoter upon stimulation of human TLR8. The cell culture supernatant SEAP reporter activity was determined using QUANTI-Blue™ kit (Cat. #: rep-qb 1, Invivogen, San Diego, Calif., USA) at a wavelength of 640 nm, a detection medium that turns purple to blue in the presence of alkaline phosphatase.

HEK293-Blue-hTLR8 cells were incubated at a density of 250,000-450,000 cells/mL in a volume of 180 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum for 24 hours. Then the HEK293-Blue-hTLR-8 cells were incubated with addition of 20 μL test compound in a serial dilution in the presence of final DMSO at 1% and perform incubation under 37° C. in a CO$_2$ incubator for 20 hours. Then 20 μL of the supernatant from each well was incubated with 180 μL Quanti-blue substrate solution at 37° C. for 1-3 hours and the absorbance was read at 620-655 nm using a spectrophotometer. The signalling pathway that TLR8 activation leads to downstream NF-κB activation has been widely accepted, and therefore similar reporter assay was also widely used for evaluating TLR8 agonist.

The compounds of the present invention were tested in the above assay for their TLR7 and TLR8 agonism activities as described herein and results are listed in Table 1. The Examples were found to have EC$_{50}$ of TLR7 agonism activities about 3 μM to about 250 μM and TLR8 agonism activities about 1 μM to about 190 μM. Particular compounds of formula (I) or (Ia) were found to have EC$_{50}$ of TLR7 agonism activities about 3 μM to about 100 μM and TLR8 agonism activities about 1 μM to about 100 μM.

TABLE 1

Activity of Compounds in HEK293-hTLR-7 and HEK293-hTLR-8 assay:

| Example No. | HEK293-hTLR-7 EC$_{50}$ (μM) | HEK293-hTLR-8 EC$_{50}$ (μM) |
|---|---|---|
| 1-A | 75 | 1.3 |
| 1-B | 101 | 55 |
| 2 | 81 | 27 |
| 3 | 7.7 | 125 |
| 4 | 3.5 | 94 |
| 5 | 3.7 | 85 |
| 6 | 250 | 4 |
| 7 | 3.4 | 2.2 |
| 8 | 82 | 185 |

What is claimed is:

1. A method for the treatment of hepatitis B virus infection, which method comprises:

administering to a patient in need thereof a therapeutically effective amount of a compound of formula (I),

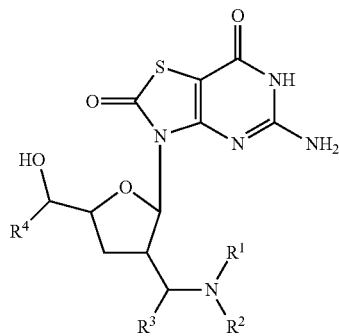

(I)

wherein:
R$^1$ is H, C$_{1-6}$alkyl, C$_{3-7}$cycloalkyl or phenylC$_{1-6}$alkyl, said phenylC$_{1-6}$alkyl being unsubstituted or substituted with one to three substituents independently selected from C$_{1-6}$alkyl and halogen;
R$^2$ is H or C$_{1-6}$alkyl;
R$^3$ is C$_{1-6}$alkyl; and
R$^4$ is C$_{1-6}$alkyl;
or a pharmaceutically acceptable salt, enantiomer, or diastereomer thereof.

2. A method for the treatment of hepatitis B virus infection, which method comprises:

administering to a patient in need thereof a therapeutically effective amount of a compound of formula (Ia),

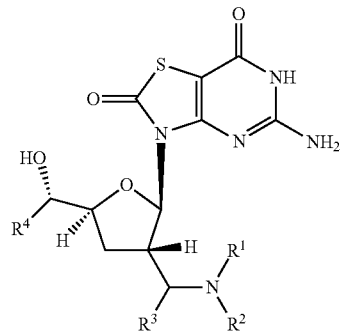

(Ia)

wherein:
R$_1$ is H, C$_{1-6}$alkyl, C$_{3-7}$cycloalkyl or phenylC$_{1-6}$alkyl, said phenylC$_{1-6}$alkyl being unsubstituted or substituted with one to three substituents independently selected from C$_{1-6}$alkyl and halogen;
R$_2$ is H or C$_{1-6}$alkyl;
R$_3$ is C$_{1-6}$alkyl; and
R$_4$ is C$_{1-6}$alkyl;
or a pharmaceutically acceptable salt, enantiomer, or diastereomer thereof.

3. A method according to claim 1, wherein:
R$^1$ is H, methyl, propyl, cyclopropyl, benzyl, fluorobenzyl, chlorobenzyl, fluorochlorobenzyl or methylbenzyl;
R$^2$ is H or methyl;
R$^3$ is methyl; and
R$^4$ is ethyl;
or a pharmaceutically acceptable salt, enantiomer, or diastereomer thereof.

4. A method according to claim 1, wherein R$^1$ is H, C$_{1-6}$alkyl or phenylC$_{1-6}$alkyl; or pharmaceutically acceptable salt, enantiomer, or diastereomer thereof.

5. A method according to claim 1, wherein R$^1$ is H, methyl or benzyl; or pharmaceutically acceptable salt, enantiomer, or diastereomer thereof.

6. A method according to claim 1, wherein R$^2$ is H; or pharmaceutically acceptable salt, enantiomer, or diastereomer thereof.

7. A method according to claim 1, wherein the compound is selected from:
5-amino-3-[(2R,3S,5S)-3-[(1S)-1-aminoethyl]-5-[(1S)-1-hydroxypropyl]tetrahydrofuran-2-yl]-6H-thiazolo[4,5-d]pyrimidine-2,7-dione;
5-amino-3-[(2R,3S,5S)-3-[(1R)-1-aminoethyl]-5-[(1S)-1-hydroxypropyl]tetrahydrofuran-2-yl]-6H-thiazolo[4,5-d]pyrimidine-2,7-dione;
5-amino-3-[(2R,3S,5S)-5-[(1S)-1-hydroxypropyl]-3-[(1R)-1-(methylamino)ethyl]tetrahydrofuran-2-yl]-6H-thiazolo[4,5-d]pyrimidine-2,7-dione;
5-amino-3-[(2R,3S,5S)-5-[(1S)-1-hydroxypropyl]-3-[(1R)-1-(propylamino)ethyl]tetrahydrofuran-2-yl]-6H-thiazolo[4,5-d]pyrimidine-2,7-dione;
5-amino-3-[(2R,3S,5S)-3-[(1R)-1-(cyclopropylamino)ethyl]-5-[(1S)-1-hydroxypropyl]tetrahydrofuran-2-yl]-6H-thiazolo[4,5-d]pyrimidine-2,7-dione;
5-amino-3-[(2R,3S,5S)-3-[(1R)-1-(benzylamino)ethyl]-5-[(1S)-1-hydroxypropyl]tetrahydrofuran-2-yl]-6H-thiazolo[4,5-d]pyrimidine-2,7-dione;
5-amino-3-[(2R,3S,5S)-5-[(1S)-1-hydroxypropyl]-3-[(1S)-1-(methyl amino)ethyl]tetrahydrofuran-2-yl]-6H-thiazolo[4,5-d]pyrimidine-2,7-dione;

5-amino-3-[(2R,3S,5S)-3-[(1S)-1-(benzylamino)ethyl]-5-[(1S)-1-hydroxypropyl]tetrahydrofuran-2-yl]-6H-thiazolo[4,5-d]pyrimidine-2,7-dione; and 5-amino-3-[(2R,3S,5S)-3-[(1R)-1-(dimethylamino)ethyl]-5-[(1S)-1-hydroxypropyl]tetrahydrofuran-2-yl]-6H-thiazolo[4,5-d]pyrimidine-2,7-dione;

or a pharmaceutically acceptable salt, enantiomer, or diastereomer thereof.

8. The method of claim 1, wherein the compound, or pharmaceutically acceptable salt, enantiomer, or diastereomer thereof is administered in a pharmaceutical composition comprising a therapeutically inert carrier.

9. A method according to claim 2, wherein:

$R^1$ is H, methyl, propyl, cyclopropyl, benzyl, fluorobenzyl, chlorobenzyl, fluorochlorobenzyl or methylbenzyl;

$R^2$ is H or methyl;
$R^3$ is methyl; and
$R^4$ is ethyl;

or a pharmaceutically acceptable salt, enantiomer, or diastereomer thereof.

10. A method according to claim 2, wherein $R^1$ is H, $C_{1-6}$alkyl or phenyl$C_{1-6}$alkyl; or pharmaceutically acceptable salt, enantiomer, or diastereomer thereof.

11. A method according to claim 2, wherein $R^1$ is H, methyl or benzyl; or pharmaceutically acceptable salt, enantiomer, or diastereomer thereof.

12. A method according to claim 2, wherein $R^2$ is H; or pharmaceutically acceptable salt, enantiomer, or diastereomer thereof.

13. The method of claim 2, wherein the compound, or pharmaceutically acceptable salt, enantiomer, or diastereomer thereof is administered in a pharmaceutical composition comprising a therapeutically inert carrier.

* * * * *